United States Patent
Hopman et al.

(10) Patent No.: US 10,363,046 B2
(45) Date of Patent: Jul. 30, 2019

(54) EXTREMITY TOURNIQUET WITH LOCKING BUCKLE

(71) Applicant: The Seaberg Company, Inc., Wilsonville, OR (US)

(72) Inventors: Lance D Hopman, Tigard, OR (US); Eric E Batdorf, Oregon City, OR (US)

(73) Assignee: The Seaberg Company, Inc., Wilsonville, OR (US)

( * ) Notice: Subject to any disclaimer, the term of this patent is extended or adjusted under 35 U.S.C. 154(b) by 302 days.

(21) Appl. No.: 15/297,937

(22) Filed: Oct. 19, 2016

(65) Prior Publication Data
US 2017/0035440 A1 Feb. 9, 2017

Related U.S. Application Data

(63) Continuation-in-part of application No. 14/324,672, filed on Jul. 7, 2014, and a continuation-in-part of application No. 14/097,018, filed on Dec. 4, 2013.
(Continued)

(51) Int. Cl.
*A61B 17/132* (2006.01)
*A44B 11/20* (2006.01)
(Continued)

(52) U.S. Cl.
CPC ........ *A61B 17/1325* (2013.01); *A44B 11/065* (2013.01); *A44B 11/125* (2013.01);
(Continued)

(58) Field of Classification Search
None
See application file for complete search history.

(56) References Cited

U.S. PATENT DOCUMENTS 1,281,653 A 10/1918 Plummer
1,679,978 A 8/1928 Konwiser
(Continued)

FOREIGN PATENT DOCUMENTS

DE 20300739 5/2003
EP 0462088 12/1991
(Continued)

OTHER PUBLICATIONS

US Patent and Trademark Office, "International Search Report and Written Opinion", for PCT App. No. PCT/US2014/016305, dated May 30, 2014, Alexandria, Virginia, 17 pages.
(Continued)

*Primary Examiner* — Robert A Lynch
(74) *Attorney, Agent, or Firm* — Chernoff, Vilhauer, McClung & Stenzel LLP

(57) ABSTRACT

A tourniquet for application to a patient's limb in an emergency situation, and a method for its application. The tourniquet includes a tension-sensing mechanism used to establish a baseline tension in a loop around an injured limb, and a tension-increasing mechanism to reduce the circumference of the loop and tighten the tourniquet as required beyond the baseline tension. The tension-sensing mechanism may be incorporated in a buckle in which when sufficient tension is developed in the loop a pin protrudes to engage and maintain tension in a strap member which is part of the loop. A latch may be incorporated in the buckle to keep it in a condition in which the pin protrudes to engage the strap and maintain the baseline tension. A release tab operable to release the latch is located where it is protected against inadvertent operation.

19 Claims, 21 Drawing Sheets

Related U.S. Application Data

(60) Provisional application No. 61/935,566, filed on Feb. 4, 2014, provisional application No. 61/733,058, filed on Dec. 4, 2012.

(51) Int. Cl.

| | | |
|---|---|---|
| *A44B 11/06* | (2006.01) | |
| *A44B 11/26* | (2006.01) | |
| *A44B 11/25* | (2006.01) | |
| *A61F 5/01* | (2006.01) | |
| *A44B 11/12* | (2006.01) | |
| *A44B 11/22* | (2006.01) | |

(52) U.S. Cl.
CPC ............ *A44B 11/20* (2013.01); *A44B 11/223* (2013.01); *A44B 11/2592* (2013.01); *A44B 11/266* (2013.01); *A61B 17/132* (2013.01); *A61B 17/1322* (2013.01); *A61F 5/0102* (2013.01); *Y10T 24/407* (2015.01)

(56) References Cited

U.S. PATENT DOCUMENTS

| | | |
|---|---|---|
| 2,113,534 A | 4/1938 | Brown |
| 2,344,021 A | 3/1944 | Bouziane |
| 2,387,428 A | 10/1945 | Brothers |
| 2,554,337 A | 5/1951 | Lampert |
| 3,171,410 A | 3/1965 | Towle, Jr. et al. |
| 3,594,872 A | 7/1971 | Kulwin et al. |
| 3,933,150 A | 1/1976 | Kaplan et al. |
| 4,049,854 A | 9/1977 | Casey et al. |
| 4,175,562 A | 11/1979 | Honan |
| 4,233,980 A | 11/1980 | McRae et al. |
| 4,390,014 A | 6/1983 | Forman |
| 4,459,979 A | 7/1984 | Lewis, Jr. |
| 4,545,370 A | 10/1985 | Welsh |
| 4,577,622 A | 3/1986 | Jennings |
| 4,580,555 A | 4/1986 | Coppess |
| 4,715,364 A | 12/1987 | Noguchi |
| 4,928,674 A | 5/1990 | Halperin et al. |
| 4,964,401 A | 10/1990 | Taigen |
| 4,991,573 A | 2/1991 | Miller |
| 5,086,759 A | 2/1992 | Buddingh |
| 5,234,459 A | 8/1993 | Lee |
| 5,307,521 A | 5/1994 | Davis |
| 5,307,811 A | 5/1994 | Sigwart et al. |
| 5,338,239 A | 8/1994 | Cleaveland |
| 5,383,893 A | 1/1995 | Daneshvar |
| 5,383,920 A | 1/1995 | Sikes |
| 5,407,422 A | 4/1995 | Matthijs et al. |
| 5,433,724 A | 7/1995 | Kawasaki et al. |
| 5,486,194 A | 1/1996 | Kawasaki et al. |
| 5,489,260 A | 2/1996 | Striano |
| 5,500,959 A | 3/1996 | Yewer, Jr. |
| 5,542,427 A | 8/1996 | Akerfeldt |
| 5,551,085 A | 9/1996 | Leighton |
| 5,643,315 A | 7/1997 | Daneshvar |
| 5,695,453 A | 12/1997 | Neal |
| 5,707,177 A | 1/1998 | Lehrer et al. |
| 5,741,295 A | 4/1998 | McEwen |
| 5,743,864 A | 4/1998 | Baldwin, II |
| 5,785,671 A | 7/1998 | Striano |
| 5,788,658 A | 8/1998 | Islava |
| 5,792,173 A | 8/1998 | Breen et al. |
| 5,799,650 A | 9/1998 | Harris |
| 5,830,168 A | 11/1998 | Finnell et al. |
| 5,893,368 A | 4/1999 | Sugerman |
| 5,968,072 A | 10/1999 | Hite et al. |
| 5,997,564 A | 12/1999 | Shehata et al. |
| 6,007,559 A | 12/1999 | Arkans |
| 6,053,883 A | 4/2000 | Schiek, Sr. |
| 6,065,166 A | 5/2000 | Sharrock et al. |
| 6,066,109 A | 5/2000 | Buser et al. |
| 6,165,147 A | 12/2000 | Morrow |
| 6,240,923 B1 | 6/2001 | Barrick |
| 6,264,673 B1 | 7/2001 | Egnelov |
| 6,352,074 B1 | 3/2002 | Okada |
| 6,503,217 B1 | 1/2003 | Gibbs et al. |
| 6,503,266 B1 | 1/2003 | Sjogren et al. |
| 6,554,784 B1 | 4/2003 | Krieg et al. |
| 6,610,022 B1 | 8/2003 | Ashbaugh et al. |
| 6,616,620 B2 | 9/2003 | Sherman et al. |
| 6,626,856 B2 | 9/2003 | Manoach |
| 6,884,254 B2 | 4/2005 | Brooks |
| 6,899,720 B1 | 5/2005 | McMillan |
| 6,939,314 B2 | 9/2005 | Hall |
| 6,998,510 B2 | 2/2006 | Buckman et al. |
| 7,008,389 B2 | 3/2006 | Krieg et al. |
| 7,094,213 B1 | 8/2006 | Cook |
| 7,329,792 B2 | 2/2008 | Buckman et al. |
| 7,574,761 B2 | 8/2009 | Davis |
| 7,677,605 B2 | 3/2010 | Cook |
| 7,776,064 B2 | 8/2010 | Jennifer et al. |
| 7,842,067 B2 | 11/2010 | Esposito |
| 7,892,253 B2 | 2/2011 | Esposito |
| 7,931,607 B2 | 4/2011 | Biondo et al. |
| 7,947,061 B1 | 5/2011 | Reis |
| 8,142,378 B2 | 3/2012 | Reis et al. |
| 8,192,383 B2 | 6/2012 | Polliack et al. |
| 8,926,536 B2 | 1/2015 | Hopman et al. |
| 9,028,435 B2 | 5/2015 | Hopman et al. |
| 2001/0053884 A1 | 12/2001 | Krieg et al. |
| 2002/0068890 A1 | 6/2002 | Schwenn et al. |
| 2002/0144343 A1 | 10/2002 | Kuiper et al. |
| 2002/0169401 A1 | 11/2002 | Walpin |
| 2003/0144343 A1 | 7/2003 | Heitsch |
| 2003/0176825 A1 | 9/2003 | Yavnai |
| 2004/0039321 A1 | 2/2004 | Krieg et al. |
| 2004/0267292 A1 | 12/2004 | Byrum et al. |
| 2005/0113866 A1 | 5/2005 | Heinz et al. |
| 2005/0267518 A1 | 12/2005 | Wright et al. |
| 2005/0273134 A1 | 12/2005 | Esposito |
| 2005/0283102 A1 | 12/2005 | Schwenn et al. |
| 2006/0135898 A1 | 6/2006 | Richardson |
| 2006/0206992 A1 | 9/2006 | Godshaw et al. |
| 2007/0022577 A1 | 2/2007 | Funo |
| 2007/0117479 A1 | 5/2007 | Weinel et al. |
| 2007/0130735 A1 | 6/2007 | Diamond |
| 2007/0282230 A1 | 12/2007 | Valderrabano et al. |
| 2008/0004555 A1 | 1/2008 | Reis et al. |
| 2008/0251807 A1 | 10/2008 | Richardson |
| 2008/0281351 A1 | 11/2008 | Croushorn et al. |
| 2009/0300888 A1 | 12/2009 | Shiue |
| 2010/0071173 A1 | 3/2010 | Hortnagl |
| 2010/0100120 A1 | 4/2010 | Perkins et al. |
| 2010/0152770 A1 | 6/2010 | Spencer |
| 2010/0179586 A1 | 7/2010 | Ward et al. |
| 2011/0034845 A1 | 2/2011 | Polliack et al. |
| 2011/0130739 A1 | 6/2011 | Fitzpatrick et al. |
| 2012/0071917 A1 | 3/2012 | McDonald et al. |
| 2012/0245500 A1 | 9/2012 | Polliack et al. |
| 2013/0110019 A1 | 5/2013 | Hopman |
| 2013/0324898 A1 | 12/2013 | Polliack et al. |
| 2014/0155797 A1 | 6/2014 | Hopman |
| 2015/0216536 A1 | 8/2015 | Hopman |
| 2015/0359542 A1 | 12/2015 | Steinbaugh et al. |

FOREIGN PATENT DOCUMENTS

| | | |
|---|---|---|
| EP | 2461772 | 12/2015 |
| EP | 3102123 | 12/2016 |
| FR | 838543 A | 3/1939 |
| GB | 2523504 A | 8/2015 |
| KR | 01-1990-0005852 B1 | 8/1990 |
| WO | 9405221 | 3/1994 |
| WO | 9702783 | 1/1997 |
| WO | 00-45756 A1 | 8/2000 |
| WO | 01060290 | 8/2001 |
| WO | 01-89433 A1 | 11/2001 |
| WO | 03-75743 A2 | 9/2003 |
| WO | 2006116413 A2 | 11/2006 |
| WO | 11-16824 A3 | 2/2011 |
| WO | 2011016824 | 2/2011 |

(56) References Cited

FOREIGN PATENT DOCUMENTS

| WO | 2013025546 A1 | 2/2013 |
|---|---|---|
| WO | 2014089243 | 6/2014 |
| WO | 2015119774 | 8/2015 |
| WO | 2018075644 | 4/2018 |

OTHER PUBLICATIONS

The International Bureau of WIPO, "Preliminary Report on Patentability" for PCT App. No. PCT/US2012/050437, dated Feb. 27, 2014, Geneva, Switzerland, 13 pages.

The International Bureau of WIPO, "Preliminary Report on Patentability" for PCT App. No. PCT/US2014/016305, dated Jun. 25, 2015, Geneva, Switzerland, 9 pages.

The International Bureau of WIPO, "Preliminary Report on Patentability" for PCT App. No. PCT/US2010/001682, dated Feb. 7, 2012, Geneva, Switzerland, 5 pages.

Blackbourne, Noncompressible Arterial Hemorrhage, and the Next Generation of "Tourniquets"?, article in Jan.-Mar. 2008 issue, PB 8-08-1/2/3, AMEDD Journal, US Army Medical Dept. Fort Sam Houston, TX, 6 pages.

Kinzel, Development of a Field Packable Junctional Tourniquet, Jan. 2, 2011, MilTech, Bozeman, MT, 16 pages.

Kragh, New Tourniquet Device Concepts for Battlefield Hemorrhage Control, Apr.-Jun. 2011 issue; The Army Medical Dept. Journal, pp. 38-47.

Seaberg Company, Int'l Search Report, PCT/US10/001682, dated Mar. 15, 2011, 5 pages.

Seaberg Company, Int'l Written Opinion, PCT/US10/001682, dated Mar. 15, 2011, 4 pages.

Seaberg Company, Int'l Search Report, PCT/US12/50437, dated Dec. 31, 2012, 16 pages.

Seaberg Company, European Search Report, EP10806730.7-2310, dated Jan. 10, 2013, 5 pages.

WIPO, International Search Report, dated Apr. 21, 2014, issued in pending International Application No. PCT/US13/073191 (WO2014/089243).

WIPO, Written Opinion of the International Searching Authority, dated Apr. 21, 2014, issued in pending International Application No. PCT/US13/073191 (WO2014/089243).

Ambu—Photos of Cervical Collar 4 pages, prior to May 2012.

PYNG Medical T-Pod Pelvic Stabilization Device Instruction Sheet single page, prior to May 2012.

European Patent Office, "Extended European Search Report" for EP App. No. 15746775.4, dated Sep. 21, 2017, Munich, Germany, 9 pages.

US Patent and Trademark Office, "International Search Report and Written Opinion", for PCT App. No. PCT/US2013/073191, dated Apr. 21, 2014, Alexandria, Virginia, 10 pages.

US Patent and Trademark Office, "International Search Report and Written Opinion", for PCT App. No. PCT/US2015/012296, dated May 4, 2015, Alexandria, Virginia, 10 pages.

European Patent Office, "Extended European Search Report" for EP App. No. 10806730.7, dated Jan. 10, 2013, Munich, Germany, 5 pages.

US Patent and Trademark Office as ISA, International Search Report issued in PCT/US2015/012296, dated May 4, 2015, 2 pages, USPTO, Alexandria, Virginia.

US Patent and Trademark Office as ISA, Written Opinion of the International Searching Authority issued in PCT/US2015/012296, dated May 4, 2015, 6 pages, USPTO, Alexandria, Virginia.

International Bureau of WIPO, International Preliminary Report on Patentability issued in PCT/US2015/012296, dated Aug. 9, 2016, 1 page, Geneva, Switzerland.

United Kingdom Intellectual Property Office, "Examination Report" for United Kingdom App. No. GB1510152.0, dated May 1, 2019, South Wales, United Kingdom, 3 pages.

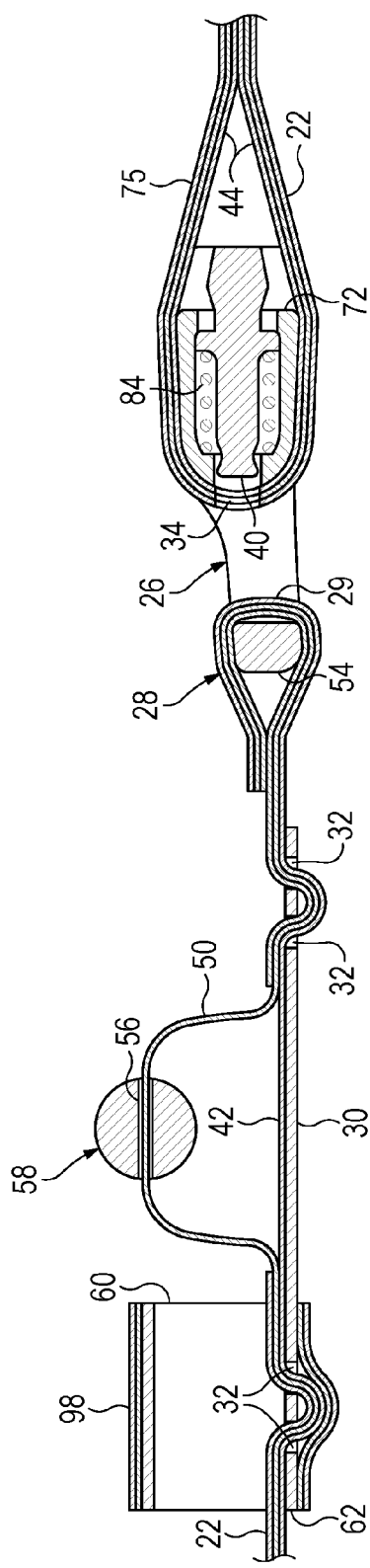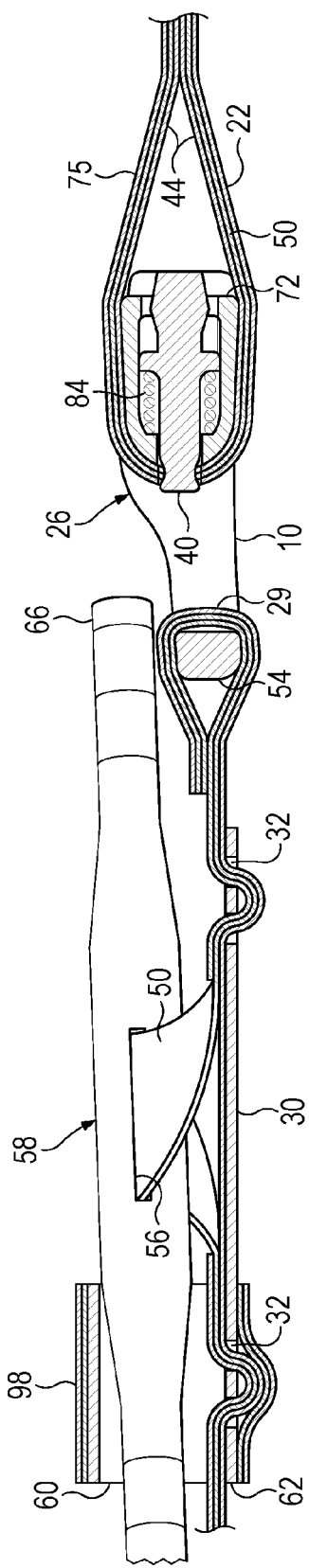
FIG. 4
FIG. 5

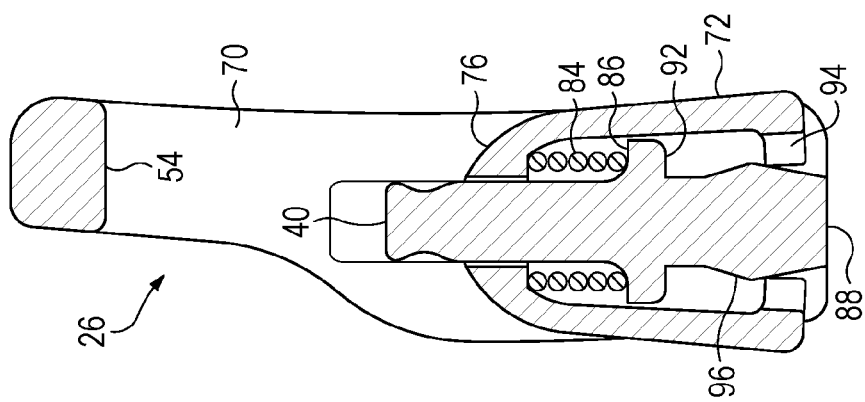
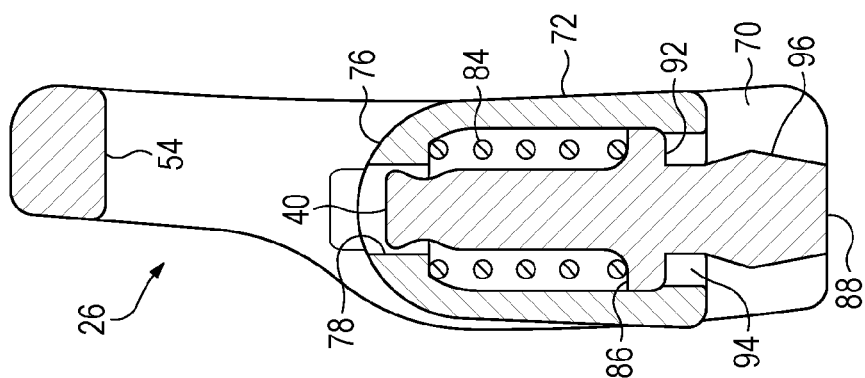
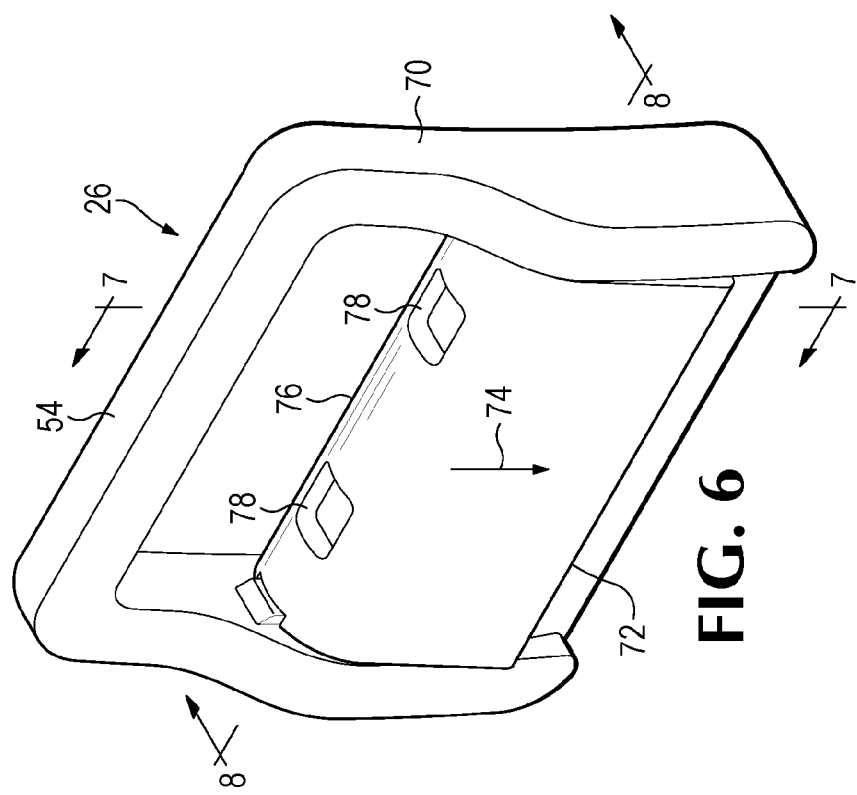

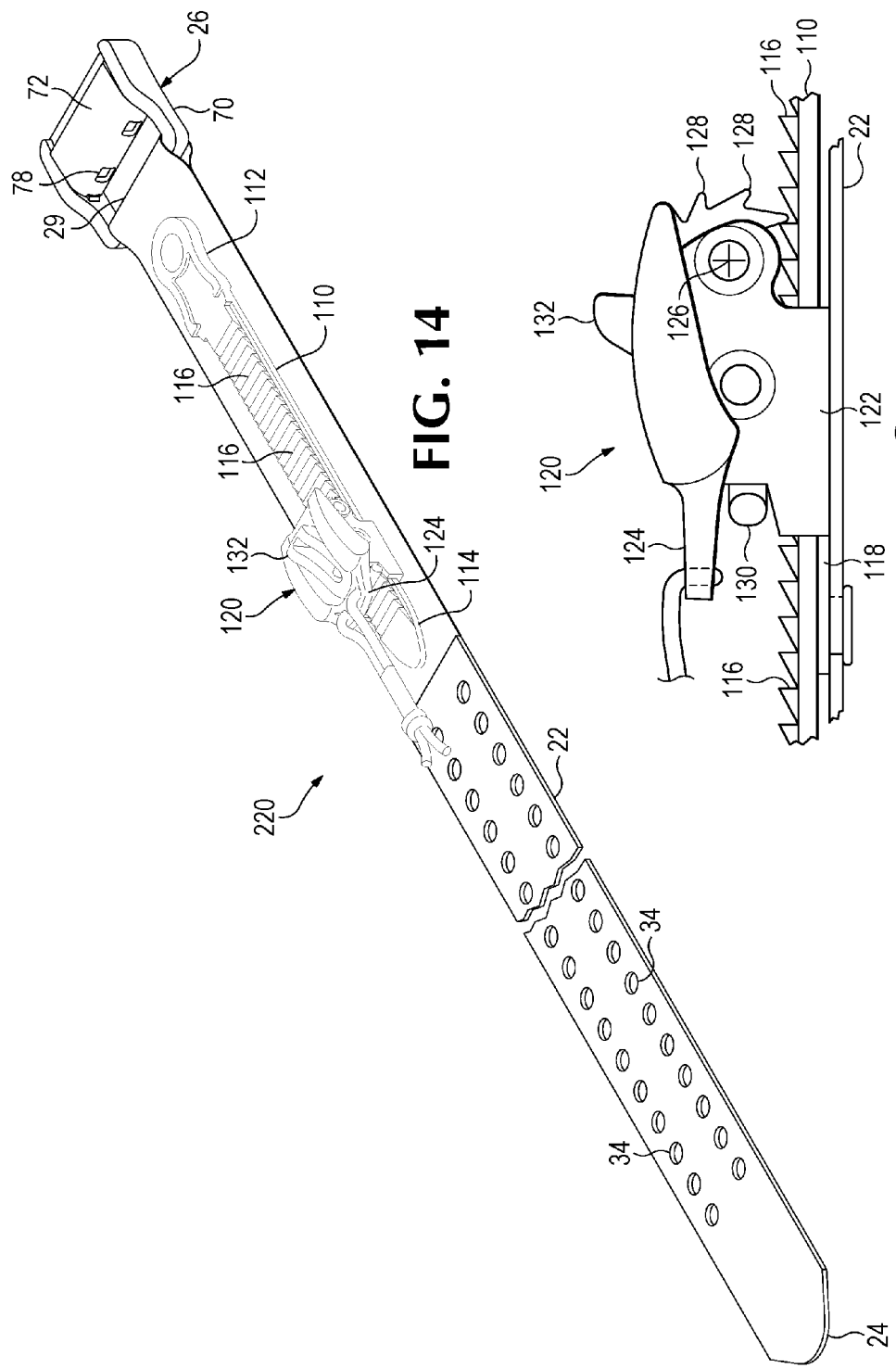

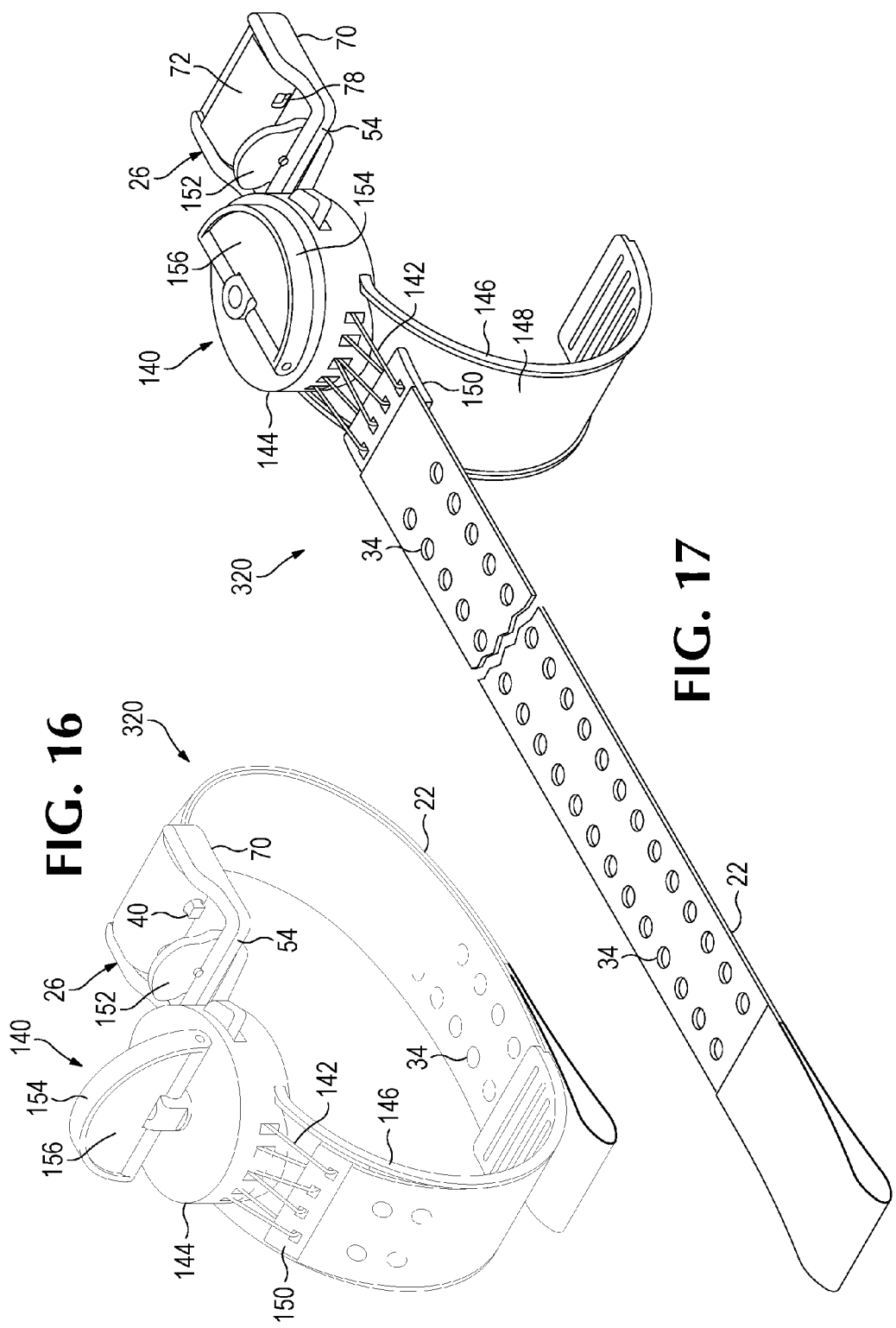

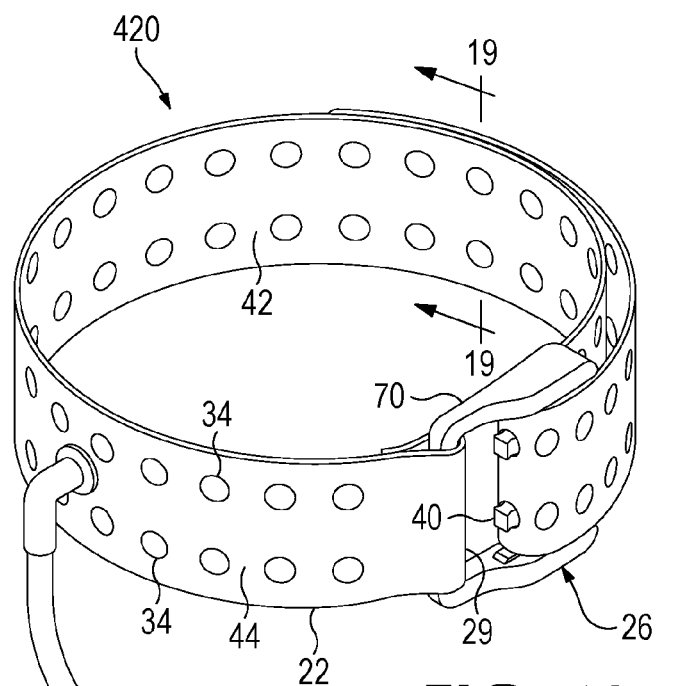
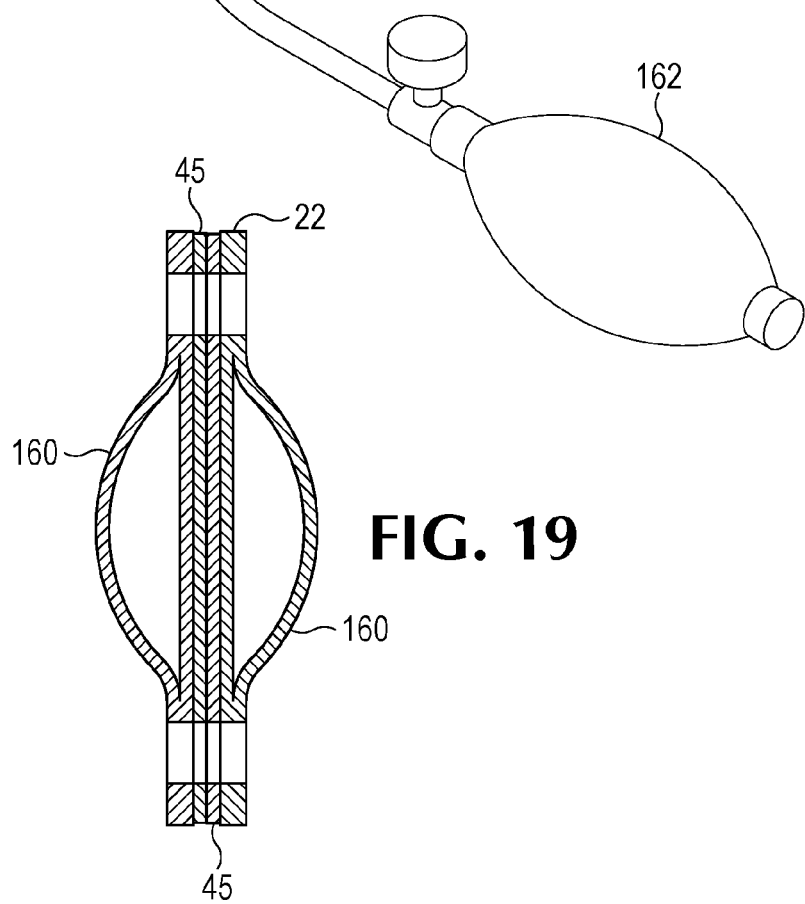
FIG. 18
FIG. 19

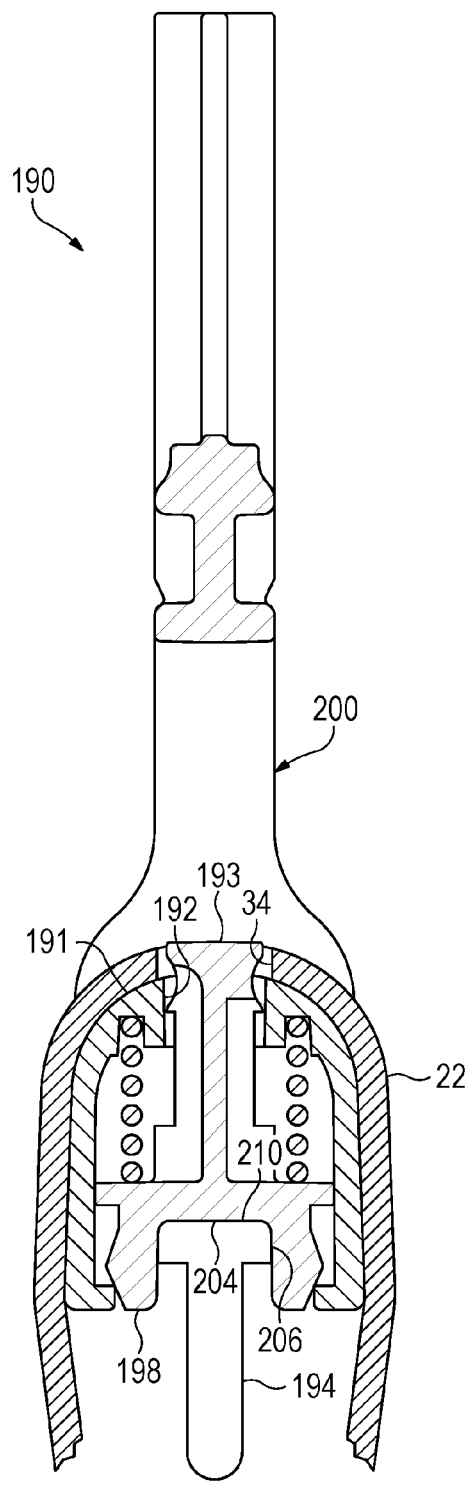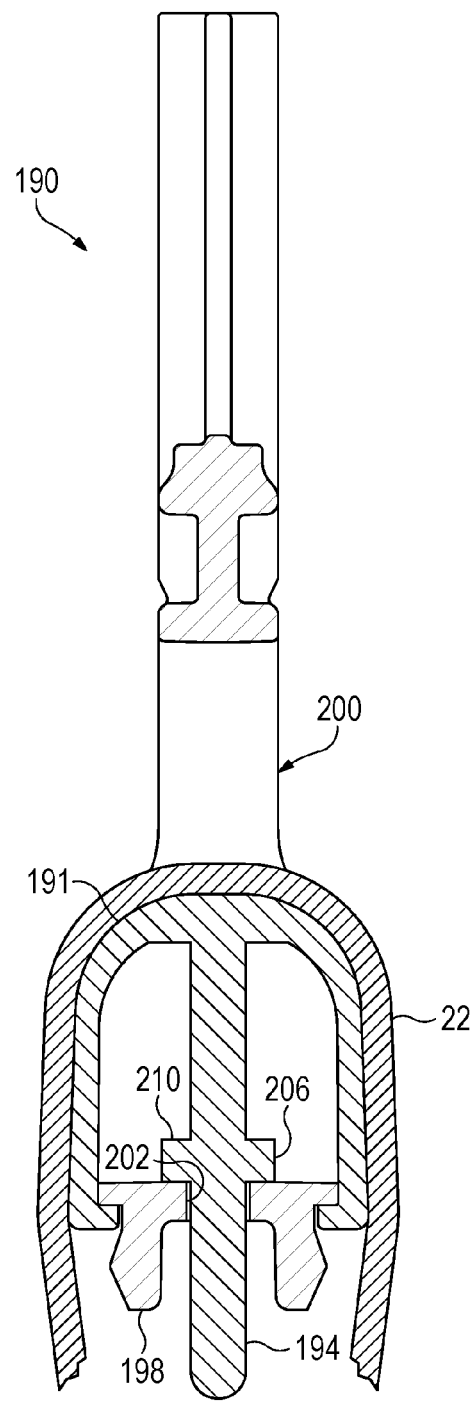
FIG. 23
FIG. 24

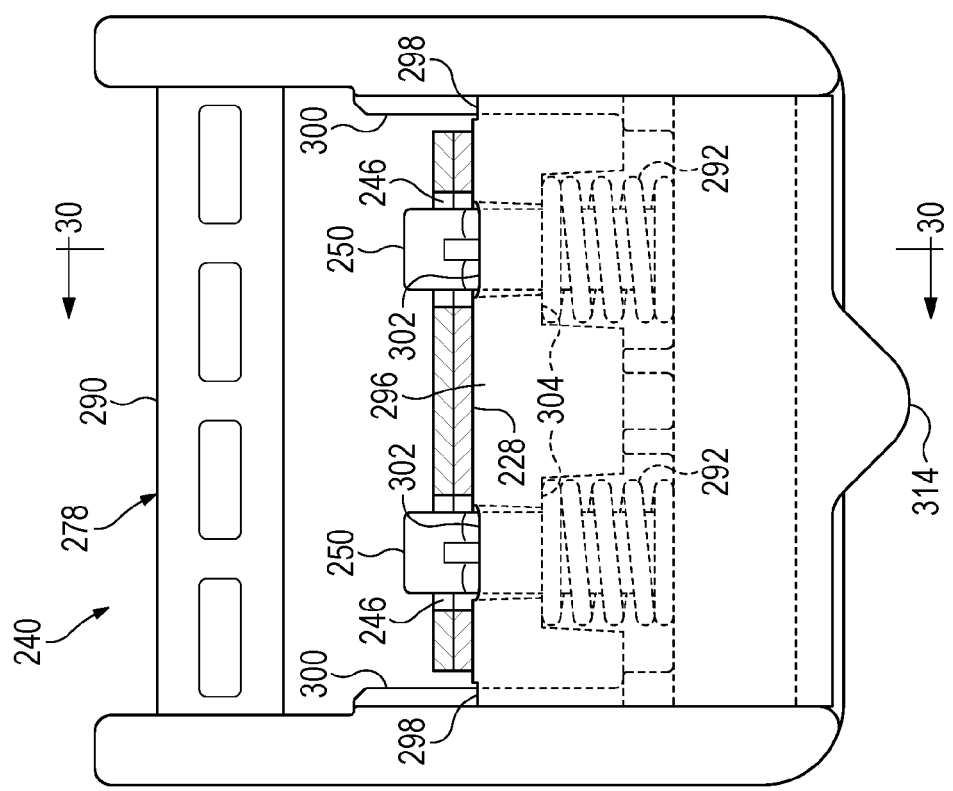
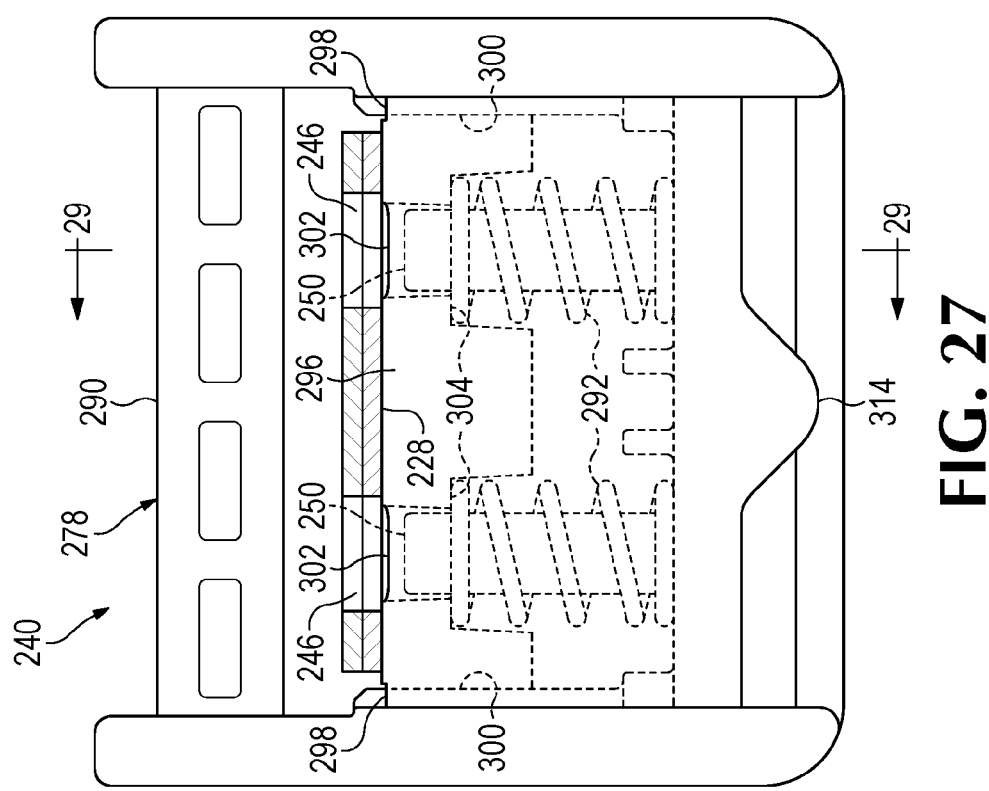

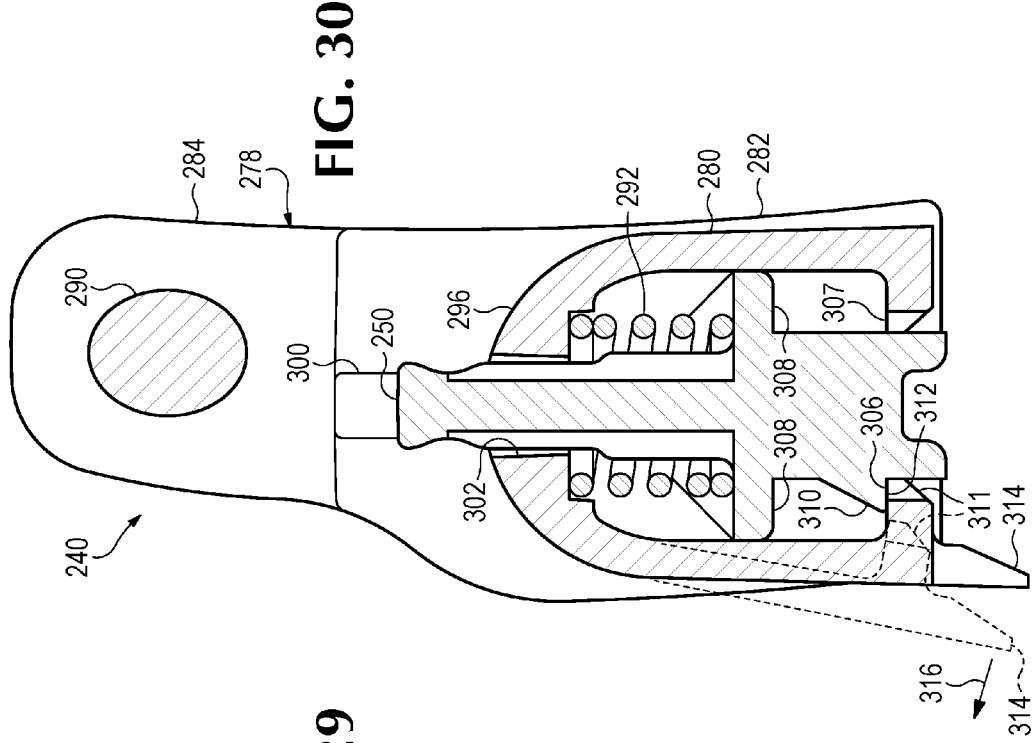
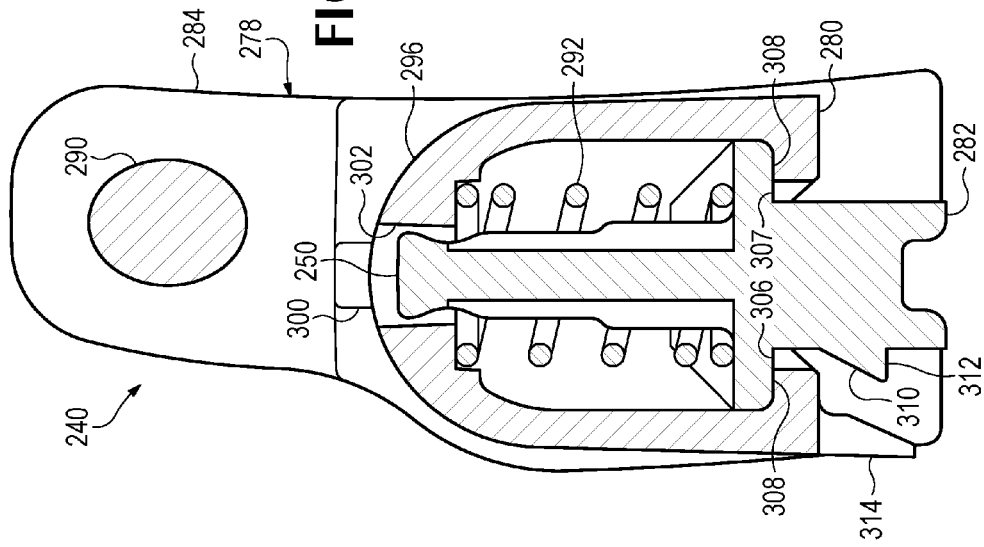

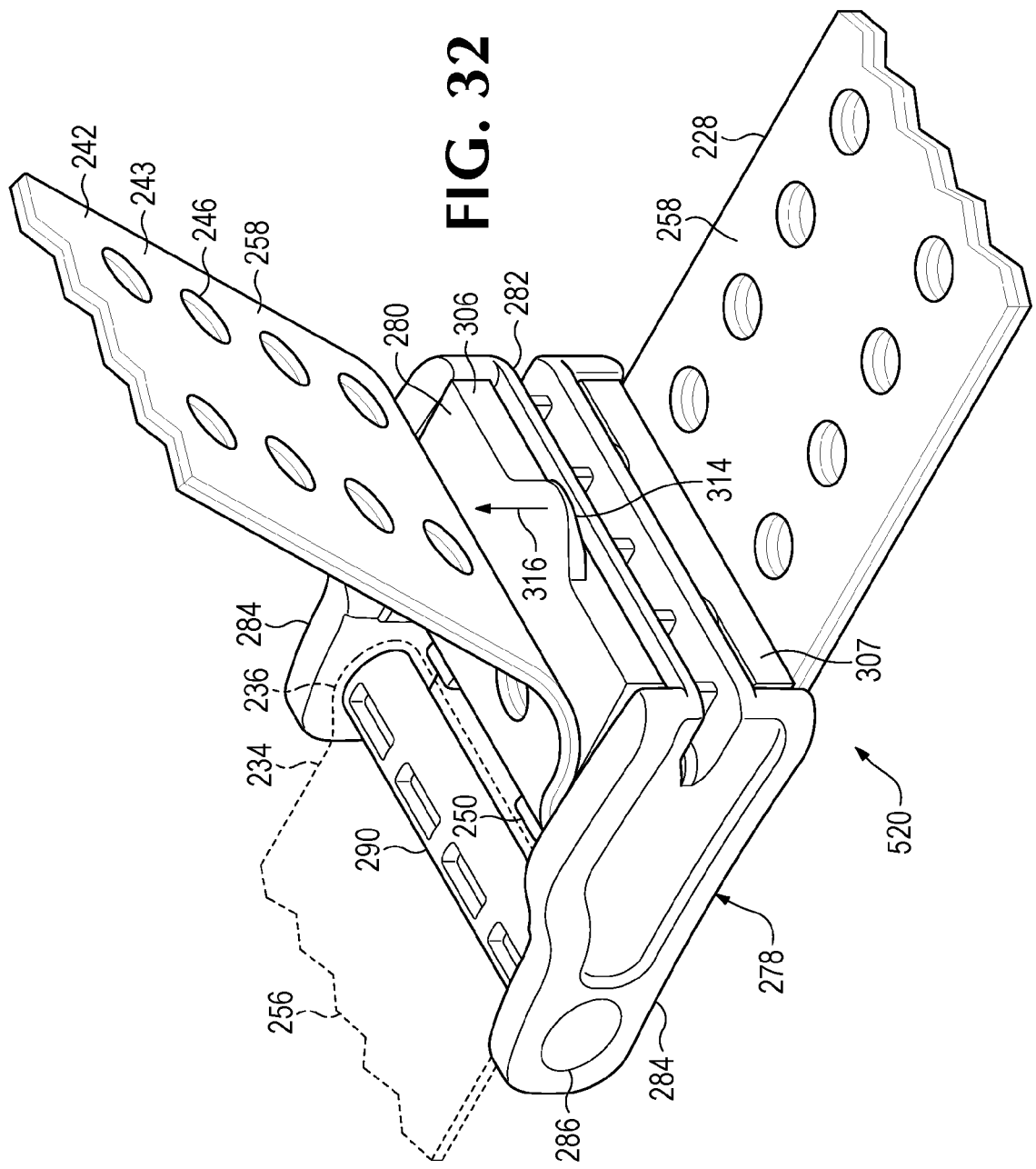

EXTREMITY TOURNIQUET WITH LOCKING BUCKLE

CROSS-REFERENCE TO RELATED APPLICATIONS

This application is a continuation-in-part of U.S. patent application Ser. No. 14/097,018, filed Dec. 4, 2013, entitled "Reversibly Engaged Force-Controlled Buckle and Pelvic Ring Support Device Incorporating Such A Buckle" and claims the benefit of U.S. Provisional Patent Application Ser. No. 61/733,058 filed Dec. 4, 2012. This application is also a continuation-in-part of U.S. patent application Ser. No. 14/324,672, filed Jul. 7, 2014, entitled "Extremity Tourniquet", and claims the benefit of the filing date of U.S. Provisional Patent Application Ser. No. 61/935,566, filed Feb. 4, 2014.

BACKGROUND OF THE INVENTION

The present application relates to tourniquets, and particularly to emergency tourniquets intended for rapid application to a patient's limb, such as a severely injured leg or arm, to minimize or stop blood loss.
Most modern emergency tourniquets are applied by using the following three similar steps:

1) Placement: A tourniquet in the form of a loop is placed in the correct position around a wounded extremity, proximal to the injury sustained by an artery or other blood vessel. The tourniquet can either be fitted as a pre-existing closed loop, or a linear strap may be placed around the limb and then formed into a closed loop. Converting from a linear strap to closed loop is most commonly achieved by routing the strap through a buckle, or by the use of one of many other mechanisms including but not limited to a quick-release buckle already in place on the strap, or a hook-and-bar fastening arrangement.

2) Gross Circumference adjustment: A strap encircling a limb is manually pulled (usually through a buckle) to tighten the loop snugly around the extremity, removing all slack and, preferably, beginning to constrict the affected limb.

3) Fine Circumference adjustment: A mechanism is used to further tighten the loop to the point where blood flow is restricted or occluded. This mechanism is most commonly in the form of a Spanish windlass, as in the CAT and SOFT-T tourniquets shown in U.S. Pat. Nos. 7,842,067 or 7,892,253 or may be one of many other mechanisms including but not limited to a ratchet as shown in U.S. Pat. No. 7,947,061, a string-and-pulley system, or a pneumatic system.

Three common shortfalls of previously known emergency tourniquets are:

1) Too much slack remains in the loop after Gross Circumference adjustment, leading to ineffectiveness of the Fine Circumference adjustment mechanism. This can result in slower application times, increased initial blood loss, or complete ineffectiveness.

2) The securement devices associated with the Gross Circumference adjustment mechanism may accidently loosen, fail, or be released after control of a hemorrhage is achieved, resulting in resumed or continued bleeding. This may be exacerbated by the fact that the Fine Circumference adjustment places an increasing force on the Gross Circumferential fastener, making the securement device more prone to failure.

3) The user is confused as to whether two tourniquets are necessary. Currently large thighs often require two tourniquets. However, the user does not know whether a first tourniquet has too much slack in it or whether it is functioning as intended. As a result, the user is not sure whether to remove and reapply the first one or put on a second.

It is desired, then, to provide an emergency tourniquet including a buckle mechanism that can be used to engage a strap forming a loop around a limb of a patient, to achieve Gross Circumference adjustment and maintain tension in the loop of the tournament encircling a patient's limb, and in which the buckle can remain engaged with the strap so that tension is retained in the loop of the tourniquet surrounding the patient's limb while the Fine Circumferential adjustment is performed.

It is thus desired to provide a tourniquet including a buckle mechanism that can be used to establish a baseline tension in a loop and maintain that desired amount of tension in the tourniquet until the tourniquet can be tightened further on a patient.

SUMMARY OF THE INVENTION

An emergency extremity tourniquet and a method of applying it disclosed herein utilize an elongate flexible strap to encircle an injured limb, forming a loop, and a tension-measuring and setting, or force-regulating, buckle that receives the strap and engages the strap securely once a predetermined amount of tension is applied to the buckle by the strap. Thereafter, while the strap extends through the buckle, an outer portion of the strap, extending outward from the buckle, is engaged with the part encircling the limb, holding the tourniquet in place around the affected limb of the patient with a certain amount of baseline tension in the strap loop. The fine adjustment of the tourniquet can then be accomplished without risk of losing tension in the strap during the fine adjustment.

The tourniquet disclosed herein thus includes a tension-measuring and setting buckle which engages a strap to form a loop once sufficient tension has been achieved in the strap. The buckle maintains a required baseline tension in a loop of the strap encircling a patient's limb. The buckle can maintain tension in the loop encircling a patient's limb, even if tension is not continuously maintained in the outer portion of the strap extending away from the buckle and which has had to be pulled through the buckle to place the loop into tension.

In one embodiment of the emergency tourniquet the tension-measuring and setting buckle consists of at least two components, a frame and a sliding block, or slider. Both the frame and the slider may be molded of suitably strong synthetic plastics resins. In such a buckle the slider is mounted movably within an opening defined by the frame, so that it can be moved toward an end of the buckle. In one embodiment of the buckle the slider's motion is resisted by a pair of springs that ordinarily keep the slider in a position obscuring the outer ends of a pair of pins or prongs so that a strap can slide along the slider within the opening defined by the frame of the buckle while tension is being developed in the loop.

Once a predetermined amount of tension has been developed in the loop increasing the tension in the strap causes the slider to move to a position with respect to the frame exposing the tips of the pins or prongs, and the pins or prongs can enter into corresponding holes provided in the strap. This sets a baseline level of tension in the loop, retaining the baseline amount of tension in the loop that was required to move the slider to the position in which the pins are exposed.

In one embodiment of the emergency extremity tourniquet disclosed herein, a tension-measuring and setting buckle includes a latch to retain the slider in a position with respect to the frame of the buckle in which the pins are exposed and can engage the strap, once a predetermined amount of tension has been developed in the strap. In such a buckle, upon movement of the slider to a particular position relative to the frame of the buckle, a latch mechanism engages portions of the slider and the frame with one another and thereafter prevents the slider from moving with respect to the frame and again obscuring the pins or prongs, even if tension in the strap is relieved to the extent that tension in the strap would no longer hold the slider in its moved position with respect to the frame.

A latch release tab is provided on the slider in a protected location, so that the latch mechanism can readily be released to disengage the slider from the frame and the slider can return to its original position in which it obscures the prongs and allows a strap to slide through the buckle. The tourniquet can thus readily be released when appropriate, but because the release tab is in a protected location inadvertent release is avoided.

In one embodiment of the emergency extremity tourniquet disclosed herein an outer end of the strap may be extended through and engaged with the tension-measuring and setting buckle before the tourniquet is applied to a limb, and the tension-measuring and setting buckle may be connected quickly with the inner end of the strap by a quick-release fastening device such as a side release buckle.

In one embodiment of the emergency extremity tourniquet disclosed herein fine adjustment of the circumference of the tourniquet is accomplished by a Spanish windlass acting on the strap.

In one embodiment of the emergency extremity tourniquet disclosed herein to accomplish fine adjustment a tensioning ratchet is arranged to act between two spaced-apart points on the strap so as to reduce the circumference of the tourniquet.

In one embodiment of the emergency extremity tourniquet disclosed herein a ratchet-equipped winding device may be used to tighten a string in a pulley-like arrangement providing a mechanical advantage to reduce the circumference of the tourniquet.

In one embodiment of the emergency extremity tourniquet disclosed herein an inflatable bladder may be used to increase radially inwardly-directed pressure on a limb on which the tourniquet has been applied.

According to the method disclosed herein, an elongate member such as a strap is placed around a limb, engaged with a tension-measuring and setting buckle to form a loop, and pulled through the buckle and tightened until the buckle senses a predetermined level of tension at which the buckle engages and immobilizes the strap or other elongate member, and an outer end part of the strap extending out beyond the buckle is fastened to the part extending around the limb. Thereafter, with the strap held stationary with respect to the tension-measuring and setting buckle, Fine Circumferential adjustment is used to tighten the tourniquet further until the tourniquet effectively stops blood flow in the limb being treated.

Application of an extremity tourniquet according to the disclosure herein can provide assurance of proper constriction of a large limb such as a patient's thigh, as application of the tourniquet involves first the step of fastening an elongate member of the tourniquet around the affected limb with a predetermined amount of tension, as regulated by a tension-measuring and setting buckle. The tension in the tourniquet is then increased by the use of a fine adjustment mechanism, and the user can determine with confidence whether a second tourniquet should be applied, as the force-controlled buckle provides assurance that a first tourniquet has been applied in a manner that assures proper function of the first tourniquet.

The foregoing and other objectives and features of the invention will be more readily understood upon consideration of the following detailed description of embodiments of the invention taken in conjunction with the accompanying drawings.

BRIEF DESCRIPTION OF THE DRAWINGS

FIG. 4 is a sectional view taken along line 4-4 in FIG. 2, but showing the condition of the secondary tightening mechanism prior to final tightening of the tourniquet.

FIG. 5 is a sectional view similar to FIG. 4, taken along line 5-5 in FIG. 3, showing the manner in which the tourniquet is retained in a final tightened condition.

FIG. 6 is an isometric view of a tension-measuring and setting buckle such as that incorporated in the tourniquet illustrated in FIGS. 1-5.

FIG. 7A is a sectional view taken along line 7-7 in FIG. 6 showing the buckle in the condition in which it is illustrated in FIG. 6.

FIG. 7B is a view similar to FIG. 7A, but showing the condition of the buckle when the strap portion of the tourniquet is under tension, as with the tourniquet in use as shown in FIG. 1.

FIG. 14 is an isometric view of the emergency extremity tourniquet shown in FIG. 13, with the tourniquet extended and in a flat configuration and the strap foreshortened so as to depict other components with greater clarity and at an enlarged scale.

FIG. 15 is a detail view of the ratchet mechanism shown as part of the tourniquet illustrated in FIGS. 13 and 14.

FIG. 16 is a view similar to a portion of FIG. 3, showing another version of the emergency extremity tourniquet disclosed herein, in which fine adjustment is accomplished by use of a string-and-pulley device.

FIG. 17 is a detail view showing the fine adjustment device shown in FIG. 16 at an enlarged scale.

FIG. 18 is a view similar to a portion of FIG. 3, showing another version of the emergency extremity tourniquet disclosed herein, in which fine adjustment may be accomplished by the use of an inflatable bladder associated with the strap portion of the tourniquet.

FIG. 19 is a sectional view taken in the direction of line 19-19 in FIG. 18.

FIG. 23 is a sectional view of the buckle shown in FIG. 20, taken along line 23-23 of FIG. 20, with the buckle in the strap-engaging, latched state in which it is shown in FIGS. 20 and 21.

FIG. 24 is a sectional view taken along line 24-24 of FIG. 20, showing the buckle in the unlatched, relaxed state in which it is shown in FIG. 22.

FIG. 27 is a top plan view of the buckle included in the portion of in extremity tourniquet shown in FIGS. 25 and 26, showing the buckle in the unlatched condition depicted in FIGS. 25 and 26, in which the strap portion of the tourniquet is free to slide through the buckle.

FIG. 28 is a top plan view of the buckle shown in FIG. 27, shown with the buckle in a latched condition and with the strap of the extremity tourniquet engaged with the buckle.

FIG. 29 is a sectional view taken along line 29-29 of FIG. 27.

FIG. 30 is a sectional view taken along line 30-30 of FIG. 28.

FIG. 32 is an isometric view of the buckle shown in FIGS. 25-31, showing the buckle in a latched condition and engaged with a portion of the strap of the extremity tourniquet.

DETAILED DESCRIPTION OF PREFERRED EMBODIMENTS

Figure 1:
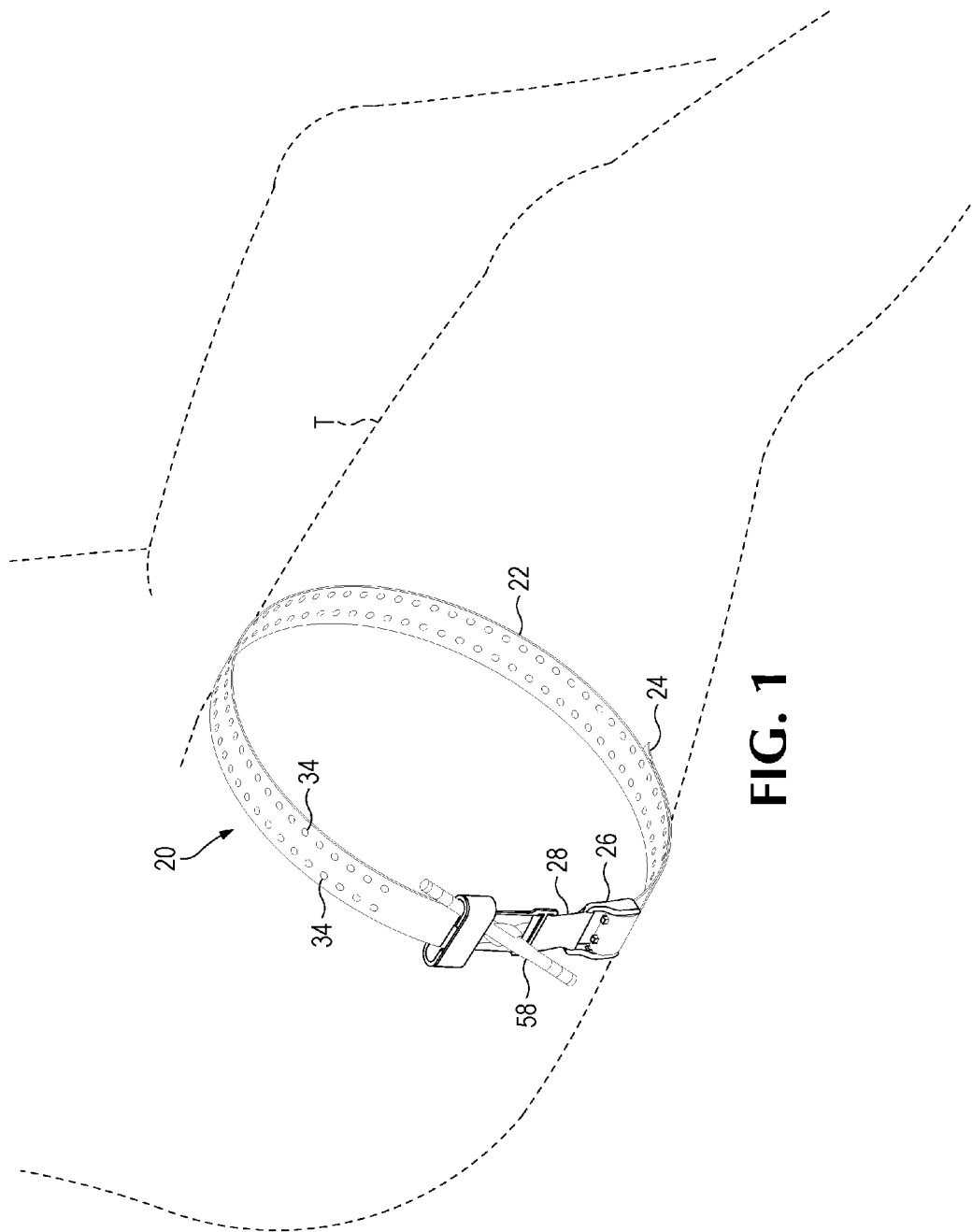
FIG. 1 is an isometric view of an extremity tourniquet attached to a person's thigh that is shown in broken line.

Referring to the drawings that form a part of the disclosure herein, a tourniquet 20 which is a first embodiment of the emergency extremity tourniquet disclosed herein is shown in FIGS. 1-9. In FIG. 1, the tourniquet 20 is shown in place on a patient's thigh T. As shown somewhat more clearly in FIGS. 2 and 3, the tourniquet 20 includes an elongate strap 22 having a first, or outer, end 24 and a buckle 26 permanently attached to its opposite, second, or inner end 28 as by a loop 29 of the strap fitted around a part of the buckle 26. A backing plate 30, of a suitably strong plastic resin or of sheet metal, for example, may be provided, and the strap 22 may be threaded through a pair of slots 32, provided at the ends of the backing plate 30, as shown in FIGS. 4 and 5.

As used herein, the term "permanently attached" means that removal and reattachment are not easily accomplished by a user and cannot be accomplished readily without the use of equipment similar to that needed for initial manufacture of the tourniquet 20.

The ribbon-like member 50 also extends through an aperture such as a slot 56 defined by and extending through a mid-length part of a rod-shaped winding member 58 located adjacent the backing plate 30 as shown best in FIGS. 4 and 5 where a portion of the ribbon-like member 50 is depicted with exaggerated length for the sake of clarity. Preferably, the length of the ribbon-like member 50 is similar to that of the outer layers 42 and 44, so that the ribbon-like member 50 ordinarily lies closely alongside the layer 42 of the strap 22. The layer 44 of the strap 22 may be interrupted near an end of the backing plate 30 to expose the ribbon-like member 50 between the pairs of slots 32 in the backing plate member 30. The winding member 58 can be utilized as a Spanish windlass to twist and wind the ribbon-like member 50 and thus effectively shorten the ribbon-like member 50, at least between the buckle 26 and the loop 29, to tighten the tourniquet 20 further after a baseline amount of tension has been established by engagement of the pins 40 of the buckle in a pair of holes 34. A retainer 60 may be attached to or may be formed as an integral part of an end 62 of the backing plate 30. The retainer 60 is oriented transversely with respect to the strap 22, with an open space 64 between opposite ends of the retainer 60, and each end is in the form of a C-shaped hook 68 large enough to receive and hold one of the opposite ends 66 of the winding member 58.

The buckle 26 is a tension-measuring and setting buckle that cooperates with the strap 22 by engaging the pins 40 in a respective pair of the holes 34 spaced apart from each other along the length of the strap 22 when a predetermined amount of tension in the strap 22 is applied to the buckle 26. As shown in FIGS. 6 through 11, the buckle 26 may include two main parts, a rigid frame 70, and a sliding block 72. The inner end portion 28 of the strap 22 is secured to bar 54 at an inner end of the frame 70 by the small loop 29 of the fabric of the strap 22, including the ribbon-like member 50. The outer end portion 75 of the strap 22 may extend through the opening defined by the frame 70, as shown best in FIGS. 4 and 5, sliding along a convexly curved contact surface or strap contact face 76 of the sliding block 72. A pair of holes 78 are defined in the sliding block 72, and the pins 40 extend from the bars of the frame 70 into the holes 78, with the ends of the pins 40 preferably below or flush with the strap contact face 76 when the buckle 26 is not in tension.

Both the frame 70 and the sliding block 72 may be molded or otherwise formed of suitably strong synthetic plastics resins. As shown in FIGS. 1-9, the rigid frame 70 includes a transversely extending bar 54 at an inner or attachment end of the buckle, which can be engaged by the small loop 29 of the strap at the inner end 28 of the strap 22. The sliding block or slider 72 is movable relative to the buckle frame 70 in a longitudinal direction as indicated by the arrow 74. The frame 70 defines an opening or passageway wide enough to receive the strap 22, which extends through the opening when the emergency tourniquet 20 is in use. When there is little tension involved the strap 22 can slide easily along the convexly curved face 76 of the slider 72 as the strap 22 is pulled to tighten the emergency tourniquet 20 about a person's limb.

Figure 2:
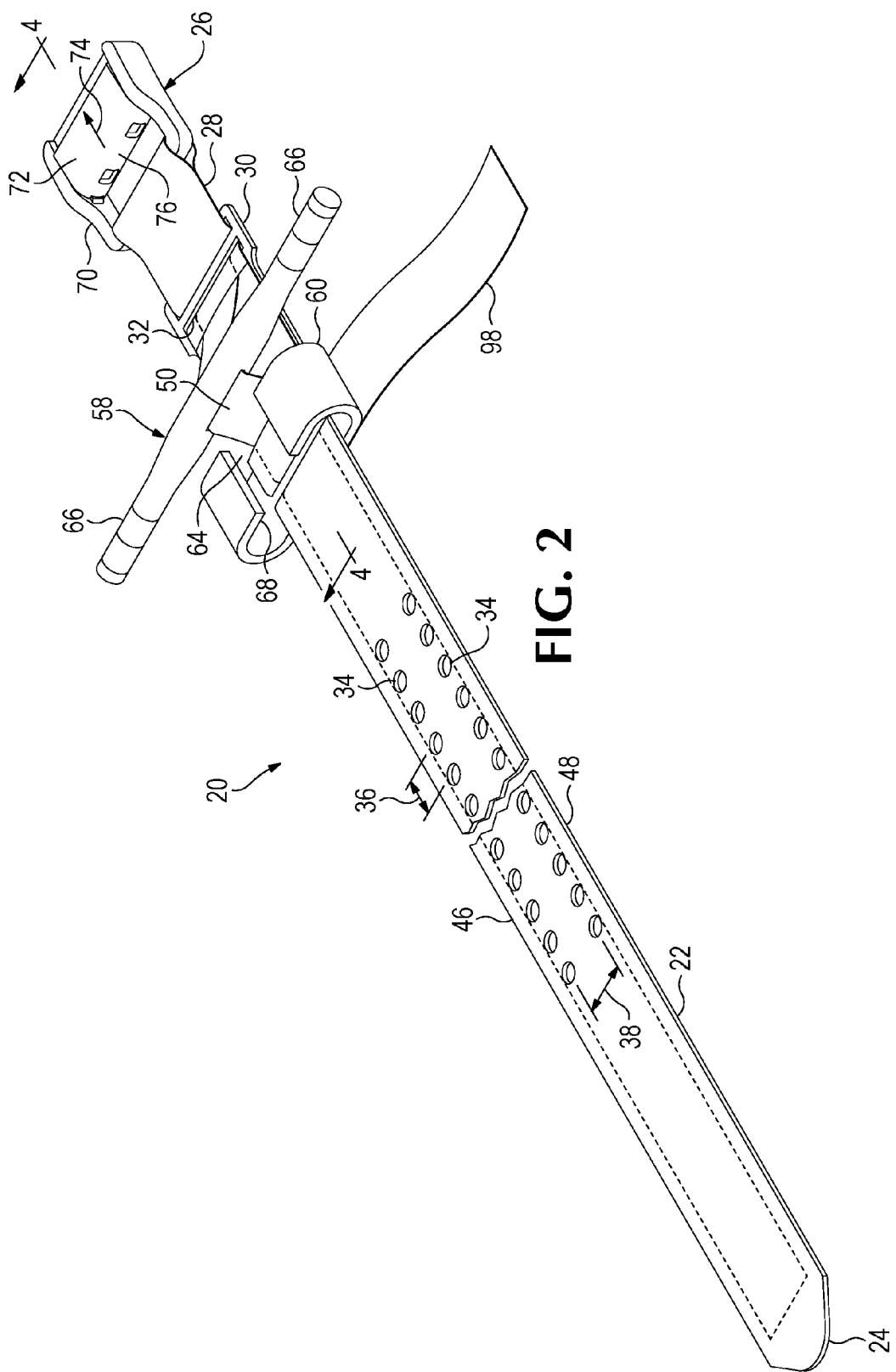
FIG. 2 is an isometric view of the tourniquet shown in FIG. 1, with the tourniquet extended in a straight and flat configuration, showing the main strap of the tourniquet foreshortened, to depict other components of the tourniquet with improved clarity at an enlarged scale.
Figure 3:
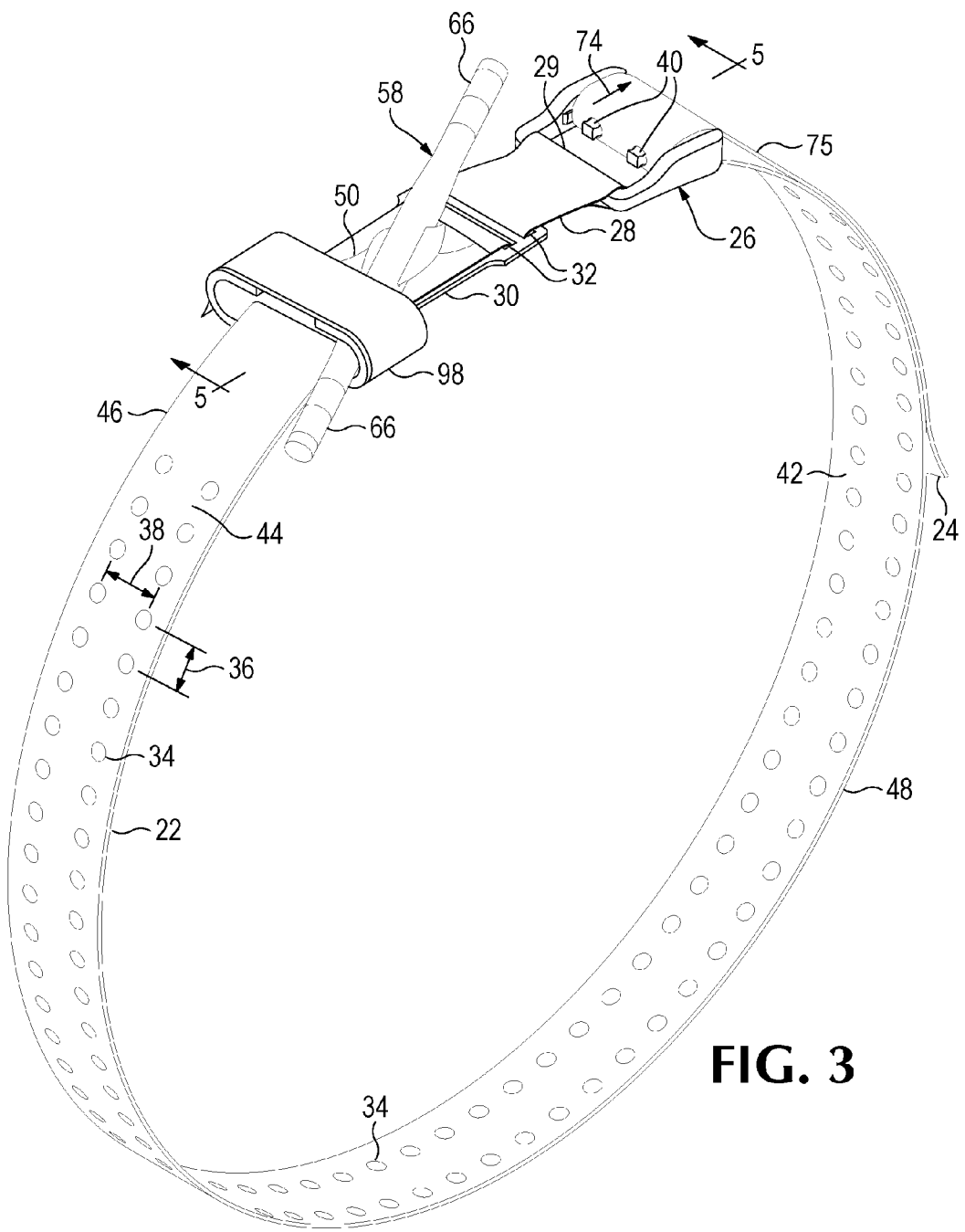
FIG. 3 is an isometric view of the tourniquet shown in FIGS. 1 and 2, showing the tourniquet in the configuration in which it is used on a patient.

The tourniquet is applied to a person's injured limb by first placing the strap 22 around the limb proximal to a hemorrhage-causing or bleeding injury. The outer end 24 of the strap is then threaded outward through the opening of the buckle 26. The outer end 24 is doubled back around the curved face 76 and pulled through the opening defined by the frame 70 of the buckle 26 so as to reduce the size of a main loop of the strap 22 extending around the limb until the tension in the main loop is sufficient to move the sliding block 72 to the right, as indicated by the arrow 74 and as seen in FIGS. 2 and 3, toward the position shown in FIG. 7A, relative to the frame 70 of the buckle 26. Substantial tension must be applied to the buckle 26 to urge the sliding block 72 to move relative to the buckle frame 70. As the strap 22 is moved further along the convex contact face 76 of the sliding block 72, the a pair of holes 34 in the strap 22 will move into alignment with the retaining pins 40 in the sliding block 72. With the strap 22 in sufficient tension against the curved face 76, once a pair of holes 34 in the strap 22 move into alignment with the holes 78 in the sliding block 72 the tension in the strap 22 moves the sliding block 72 so that the pins 40 protrude from the holes 78 and into the holes 34. As the pins 40 extend into a pair of holes 34, they engage the strap 22, and prevent it from moving relative to the buckle 26, apart from any differences in size between the pins 40 and the holes 34. The holes 34 in the strap 22 may have a slightly larger diameter than the largest transverse dimension of each of the pins 40, so that engagement of the pins 40 in the holes 34 occurs easily and smoothly at the desired tension in the strap 22.

The user then can secure the outer end portion 24 of the strap by pressing the outwardly extending pulled part 75 of the strap 22 located near the buckle 26 against the exterior of the main loop so that the fastener surfaces on the layer 44 of the strap 22 engage one another, or so that such other fastening material or devices that are provided are activated, to prevent the part 75 of the strap extending outward beyond the buckle 26 from moving relative to the portion of the strap 22 forming the main loop around the injured limb, and to retain the strap 22 at the desired location with respect to the sliding block 72 with the pins 40 engaged in holes 34.

Thus, in the Gross Circumference adjustment phase of applying the emergency terminal tourniquet 20, holes 34 in the strap 22 are engaged, and holes in the ribbon-like member 50, if present, may be engaged by the prongs, or pins, 40 of the buckle 26, once a predetermined baseline level of tension is reached in the strap 22, pushing the sliding block 72 against the force of the springs 84. It will be appreciated that a closer longitudinal spacing distance 36 between holes 34 should provide greater accuracy of the baseline tension.

Figure 8:
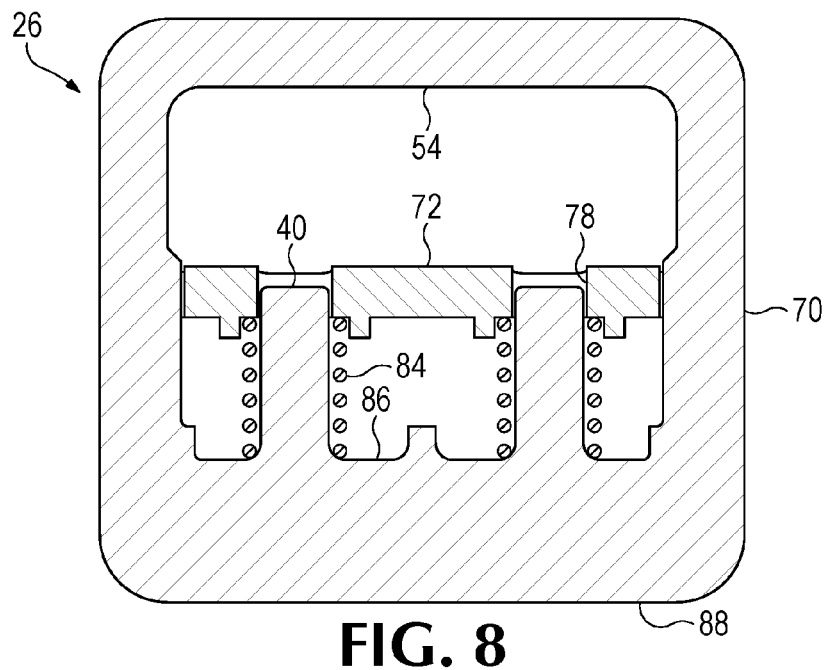
FIG. 8 is a sectional view taken along 8-8 in FIG. 6, showing the construction of a first version of the buckle incorporating a pair of helical springs.
Figure 9:
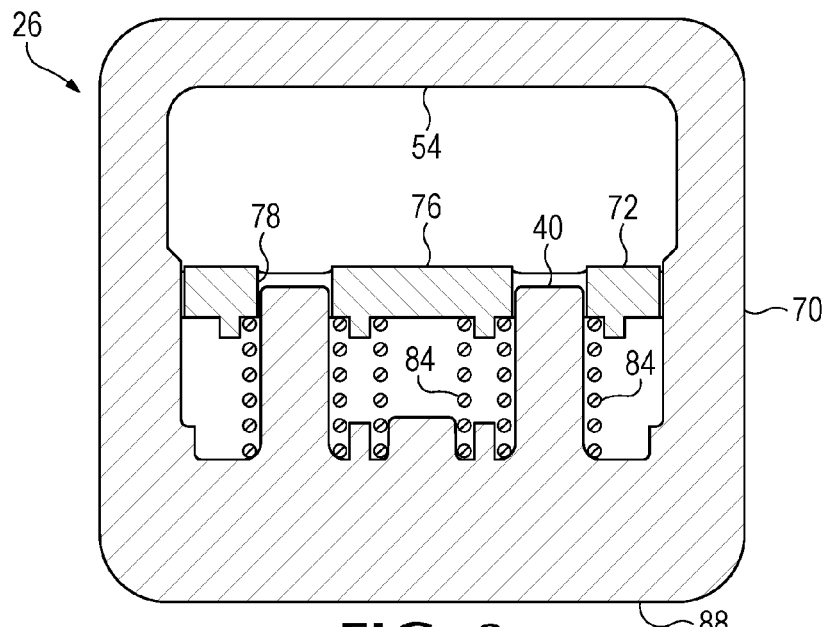
FIG. 9 is a sectional view similar to FIG. 8, but showing a slightly different version of the buckle incorporating an additional spring.

FIGS. 4 and 5 show a spring 84 positioned around one of the pins 40. An identical spring 84 may be used on the other pin 40, as shown in FIG. 8, or there may be three springs 84, as shown in FIG. 9, if desired to assure a needed amount of tension in the tourniquet 20. Suitable seats 86 for the springs 84 may be provided on the base of the frame 70 and the interior of the sliding block 72. The springs 84 are compressed somewhat when the sliding block 72 is in its fully extended position shown in FIGS. 4, 6, and 7A, to set a baseline tension that must be applied to the buckle 26 by tension in the strap 22 before the sliding block 72 begins to move relative to the buckle frame 70. Substantial tension must be applied to the buckle 26 when the tourniquet 20 is in use, urging the sliding block 72 to move in opposition to the springs 84 before the sliding block 72 begins to move relative to the buckle frame 70. The internal springs 84 are compressed further as the sliding block 72 moves to the right as seen in FIG. 4, toward the position shown in FIGS. 5 and 7B, when there is sufficient tension in the strap 22.

Flanges 92 extend along opposite sides of the base 88 of the buckle frame 70 and are engaged by inwardly projecting retaining lips 94 on the two sides of the sliding block 72 when the buckle 26 is not in tension and the sliding block 72 is in the fully extended position as shown in FIGS. 4 and 6. The flanges 92 and retaining lips 94 thus carry and sustain the compressive force of the springs 84, keeping them compressed when there is no tension applied to the buckle 26. The opposite sides of the sliding block 72 can be sprung apart from each other as the slider is placed into position within the opening defined by the frame 70, with the lips 94 passing over the flanges 92 to reach the position shown in FIG. 7A.

When the buckle 26 is in sufficient tension, the sliding block 72 moves toward the position shown in FIG. 7B from the position shown in FIG. 7A, and the retaining lips 94 ride up and over the tops of the ramps 96 beneath the flanges 92. Movement of the sliding block 72 may then create an audible click, as the sliding block 72 moves relative to the frame 70 and the pins 40 extend through the sliding block 72 and into the holes 34, indicating to the user that the buckle 26 is engaged with the strap 22. Thereafter the inwardly directed elastic force in the sides of the sliding block 72 presses the lips 94 against the ramps 96 and may help somewhat to keep the sliding block 72 in its depressed position, with the pins 40 engaged in the holes 34. A slightly lower amount of tension in the main loop of the tourniquet 20 between the pins 40 and the loop 29 is then sufficient to keep the sliding block 72 in the rightwardly depressed position, once the pins 40 have become engaged in the holes 34 as shown in FIGS. 3 and 5.

Thus, when the proper initial amount of tension as determined by the springs 84 in the buckle 26 has been reached in the main loop portion of the emergency terminal tourniquet 20 wrapped around an injured limb of a patient, the pins 40 of the buckle 26 will engage the strap 22, and so long as tension in the main loop portion of the strap 22 extending from the bar 54 of the buckle 26 and around the limb is not more than slightly reduced, the pins 40 will remain engaged in the holes 34.

Figure 10:
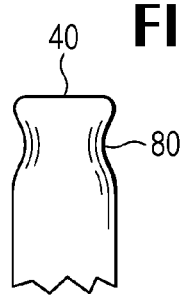
FIG. 10 is a sectional detail view of an end portion of one of the strap-retaining pins of the buckle.
Figure 11:
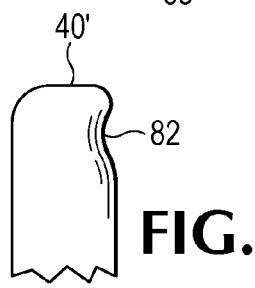
FIG. 11 is a view similar to that of FIG. 10 showing an end portion of a strap-retaining pin having a somewhat different configuration.

Referring to FIGS. 10 and 11, the pins 40 of the buckle 26 may have outer tips shaped as shown in FIGS. 7A and 7B, with a shallow groove 80 extending around each pin near its tip, as shown in FIG. 10. Alternatively, as shown in FIG. 11, a shallow groove 82 may extend partially around the tip of a pin 40' on only the side against which a hole 34 would pull when the strap 22 is under tension. The groove 82 thus would be on the upper side of a pin 40' oriented as illustrated in FIG. 3 wherein the main loop of strap 22 of the tourniquet is pulling in a primarily downward direction as illustrated in FIG. 3.

The mated fastener material on the layer 44 will hold the strap 22 engaged with the buckle 26 at the location where the pins 40 of the buckle 26 are engaged in a pair of holes 34 along the strap 22. Accordingly, engagement of the fastener material maintains sufficient tension in the outer, or pulled, free portion 75 of the strap 22 to keep the pins 40 of the buckle 26 engaged in a pair of holes 40 in the strap 22, to maintain a consistent predetermined initial application, or baseline, amount of tension, in the tourniquet 20. The baseline tension in the main loop of the strap 22 around a patient's limb may acceptably be in the range of about 6 pounds to about 33 pounds. A baseline tension of about 18 pounds has been found to be satisfactory, in that it allows tension to be increased sufficiently without exceeding the range of adjustment available. As shown in FIGS. 1 and 3, the effective circumference of the emergency terminal tourniquet is thus maintained at an initial size providing compression of an injured limb, as a reliable basis with a known baseline tension for additional Fine Circumferential tightening of the emergency extremity tourniquet 20 to achieve termination of hemorrhaging.

With the emergency extremity tourniquet 20 in place on a patient's injured limb with the strap 22 engaged with the buckle 26 so as to provide the predetermined baseline amount of tension, further tightening or Fine Circumferential adjustment of the tourniquet 20 can be provided by utilizing an included fine adjustment mechanism. As shown in FIGS. 1 through 5, a winding member 58 can be used as a Spanish windlass to tighten the ribbon-like member 50. Turning the winding member 58 as shown in FIGS. 3 and 5 shortens the portion of the ribbon-like member 50 between the layers 42 and 44 of the strap 22, at least between the pins 40 and the bar 54 of the buckle 26, further tightening the tourniquet 20 around the injured limb, while leaving the outer layers 42 and 44 of the strap 22 in place, albeit with reduced tension. Once bleeding from an open wound or other evidence of hemorrhage in a distal portion of the patient's limb has been terminated, one of the end portions 66 of the winding member 58 can be engaged in one of the hooks 68 of the retainer 60 to prevent unwinding of the ribbon-like member 50 and maintain the increased tension in the tourniquet 20.

A retainer strap 98 can then be applied to surround the retainer 60. The retainer strap 98 can held in place by a suitable fastener such as a pressure-sensitive adhesive, hook-and-loop fastener material, snaps, or another device. Preferably, the retainer strap 98 has an outer surface that can readily receive and legibly retain information written with a normally available writing instrument, so that the time of application of the tourniquet 20, for example, can be recorded for the use of medical personnel at a later time as when the tourniquet 20 has been applied during triage.

Consistent baseline tension as provided by tightening the strap 22 until the buckle 26 operates as described above means less Fine Circumference adjustment is needed, and that the amount of such fine adjustment may be more consistent than when the needed initial tension in a tourniquet is simply estimated by the user. Fewer Spanish windlass turns results in faster tourniquet application, and less variation user to user and patient to patient. A more consistent required number of windlass turns results in easier user training and more intuitive use of a tourniquet capable of providing such a predetermined amount of baseline tension.

When the tourniquet 20 is first applied under baseline tension and the free portion 75 of the strap 22 is secured, the prongs or pins 40 may or may not later retract (as when the tension diminishes slightly through tissue or textile relaxation). As the Spanish windlass is tightened, the prongs or pins 40 protrude again and positively engage the holes 34. The tourniquet 20 cannot be removed thereafter without unwinding the Spanish windlass. In other words, as the Fine Circumference adjustment force is increased, the risk of the tourniquet loosening or becoming detached decreases.

Figure 12:
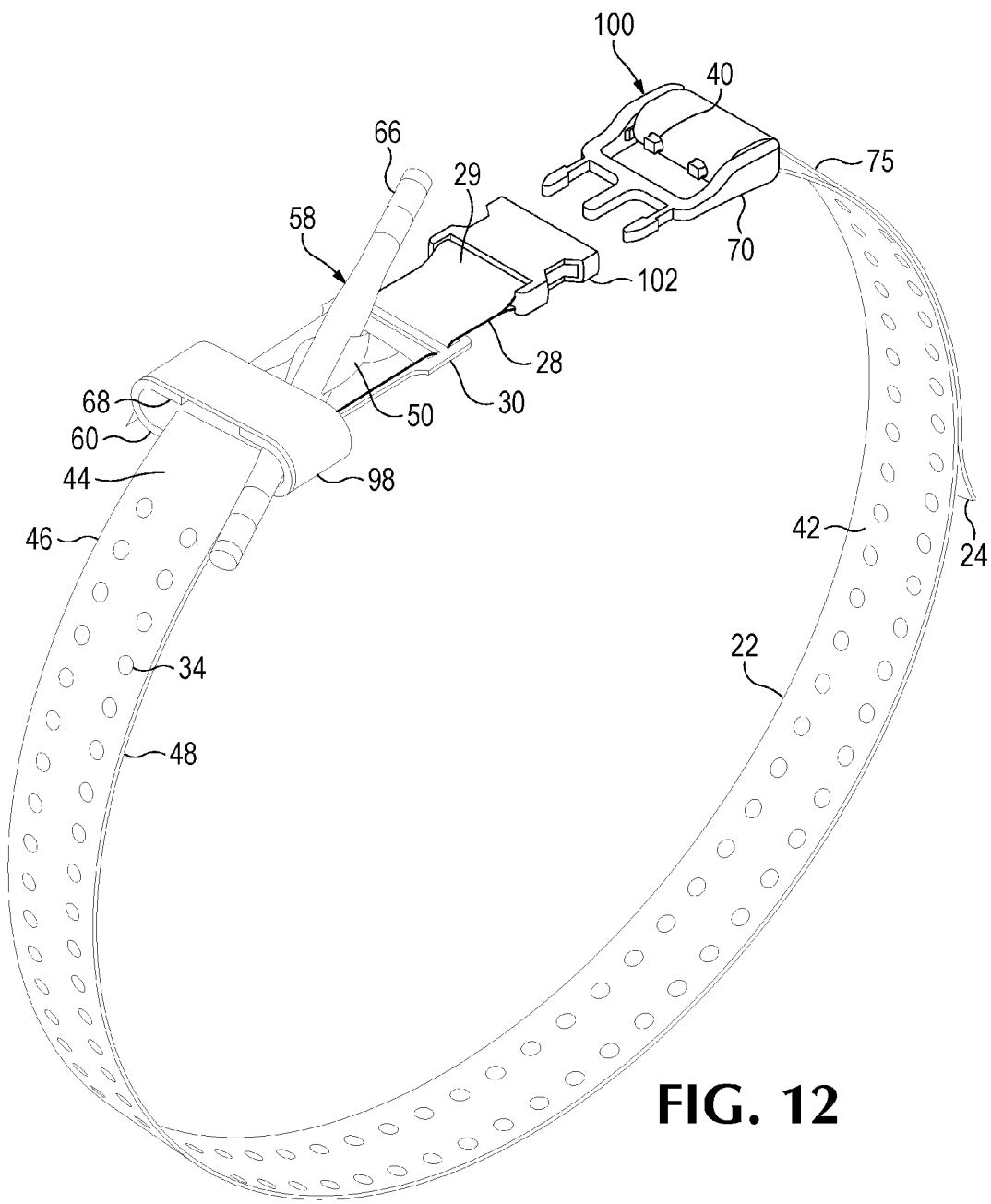
FIG. 12 is a view similar to a portion of FIG. 3, showing another version of the emergency extremity tourniquet disclosed herein, in which the force-regulating, tension-measuring and setting buckle is attached to the strap in a different manner.

As shown in FIG. 12, a force-regulating buckle 100, similar to the buckle 26, may be attached to the second, or inner, end 28 of the strap 22 so as to be separated easily from it. As a benefit of this possibility, the outer end 24 and adjacent part 75 of the strap 22 can be threaded through the buckle 100, with the parts of the strap 22 held together and immobilized with respect to each other by the fastening material on the outer layer 44, and thus kept ready for quick initial application. For example, the female part of a side release buckle 102 may be attached to the inner end 28 of the strap by a sewn loop 29, and the force-regulating buckle 100 can be connected to or disconnected from the inner end 28 of the strap by operation of the side release buckle 102. Initial application of the tourniquet 20 to a patient may then be accomplished simply by fastening the side release buckle, resulting in the outer end free portion 75 of the strap being immediately available to tighten the main loop of the tourniquet 20 around the patient's limb until the force-regulating buckle 100 detects sufficient baseline tension present in the loop and engages its pins 40 into the holes 34 in the strap 22. Instead of a side release buckle, other easily connected arrangements, such as a hook and a loop, may be used to attach the buckle to the inner end 28 of the strap 22.

The beneficial effects of using the force-regulating buckle 26 or 100 can also be obtained in the emergency extremity tourniquet 20 using other mechanisms for Fine Circumference adjustment, as shown in FIGS. 13 through 19.

Figure 13:
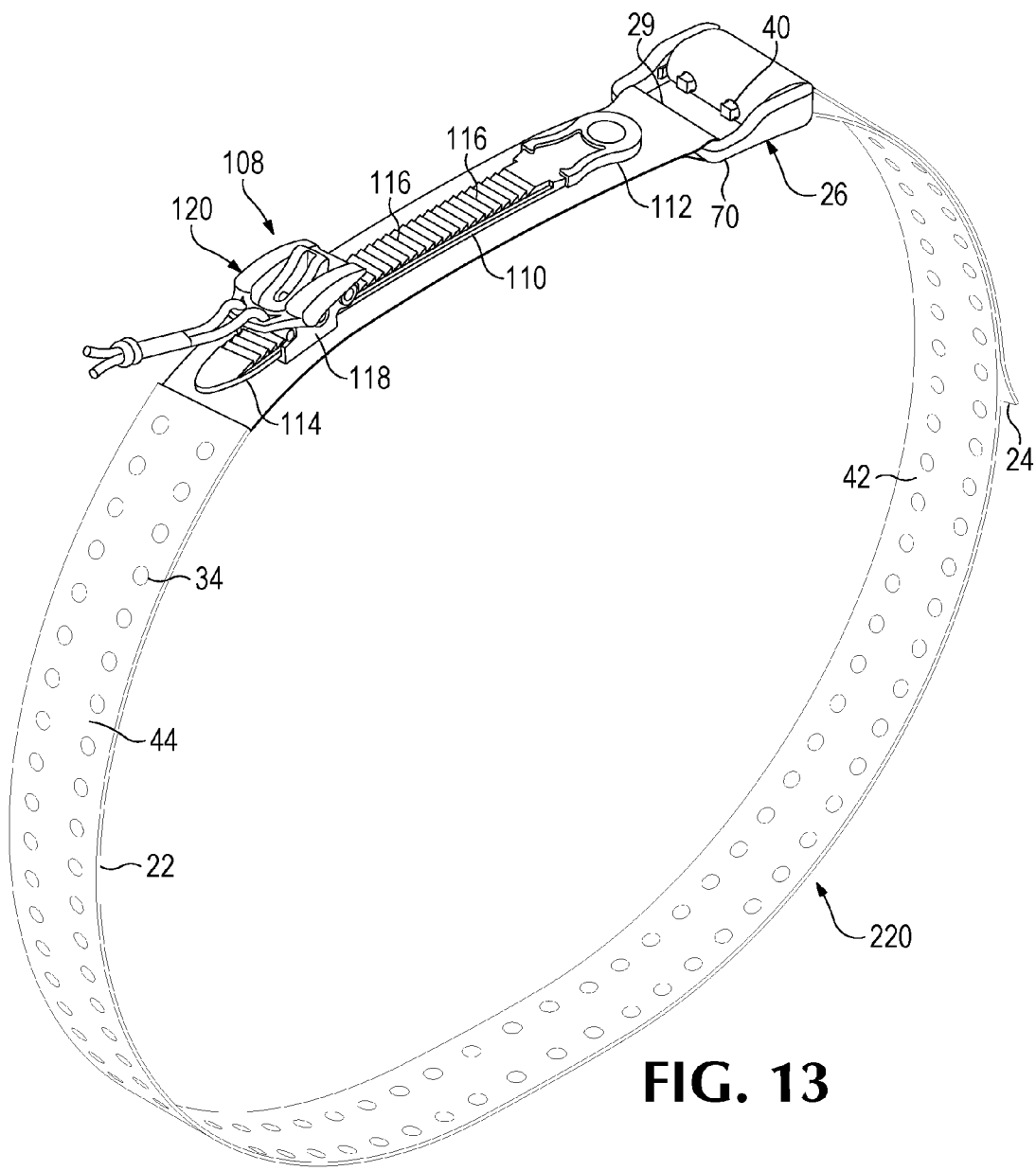
FIG. 13 is a view similar to a portion of FIG. 3, showing another version of the emergency extremity tourniquet disclosed herein, in which fine adjustment is accomplished by use of a ratchet device.
Figure 20:
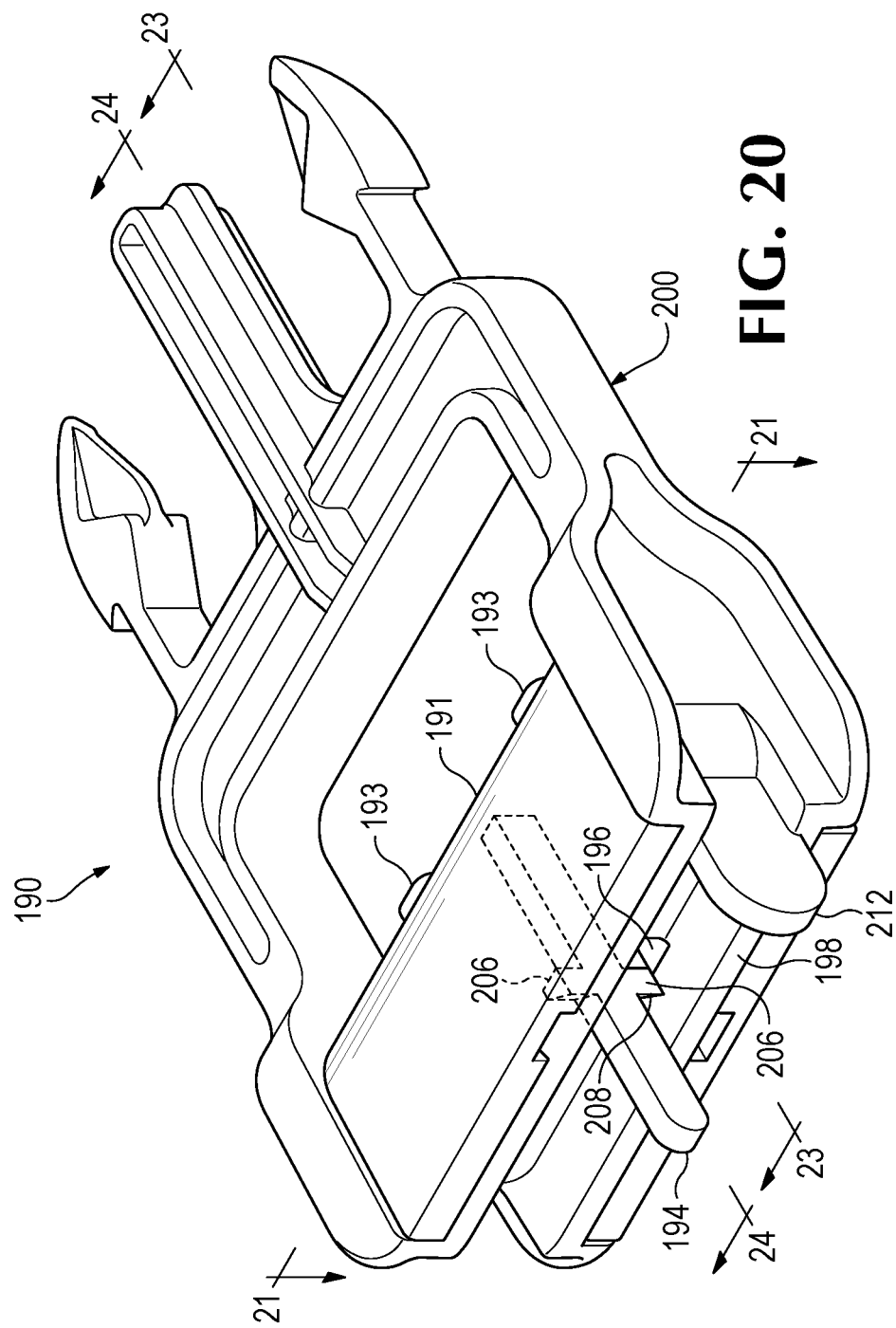
FIG. 20 is an isometric view of a buckle that is yet another embodiment of an aspect of the invention disclosed herein.
Figure 21:
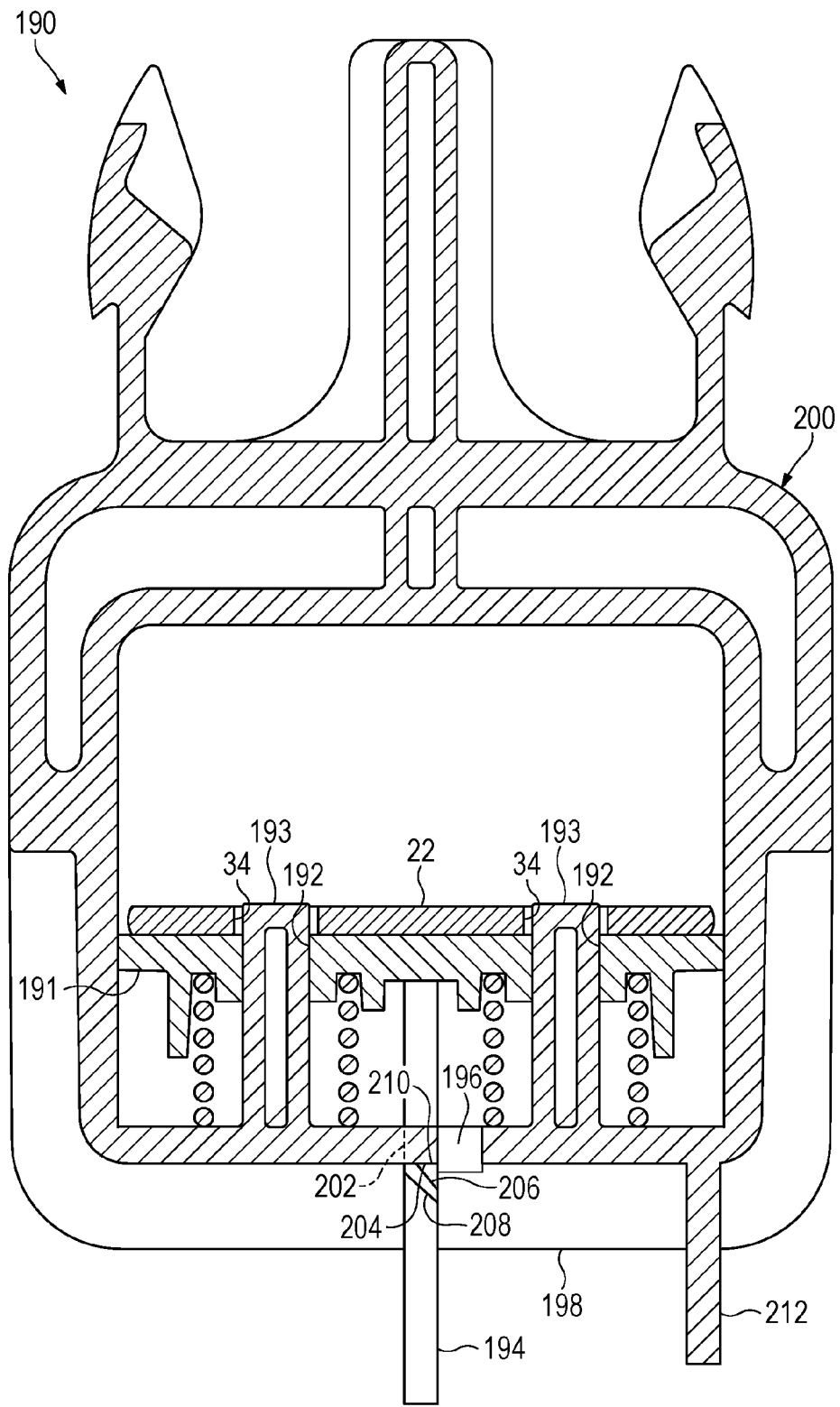
FIG. 21 is a sectional view of the buckle shown in FIG. 20, taken along line 21-21, showing the buckle latched in a strap-engaging condition, as when it has been subjected to an amount of tension sufficient to cause the strap-retaining pins of the buckle to engage a hole defined in the strap that is part of the tourniquet shown in FIGS. 1-3.
Figure 22:
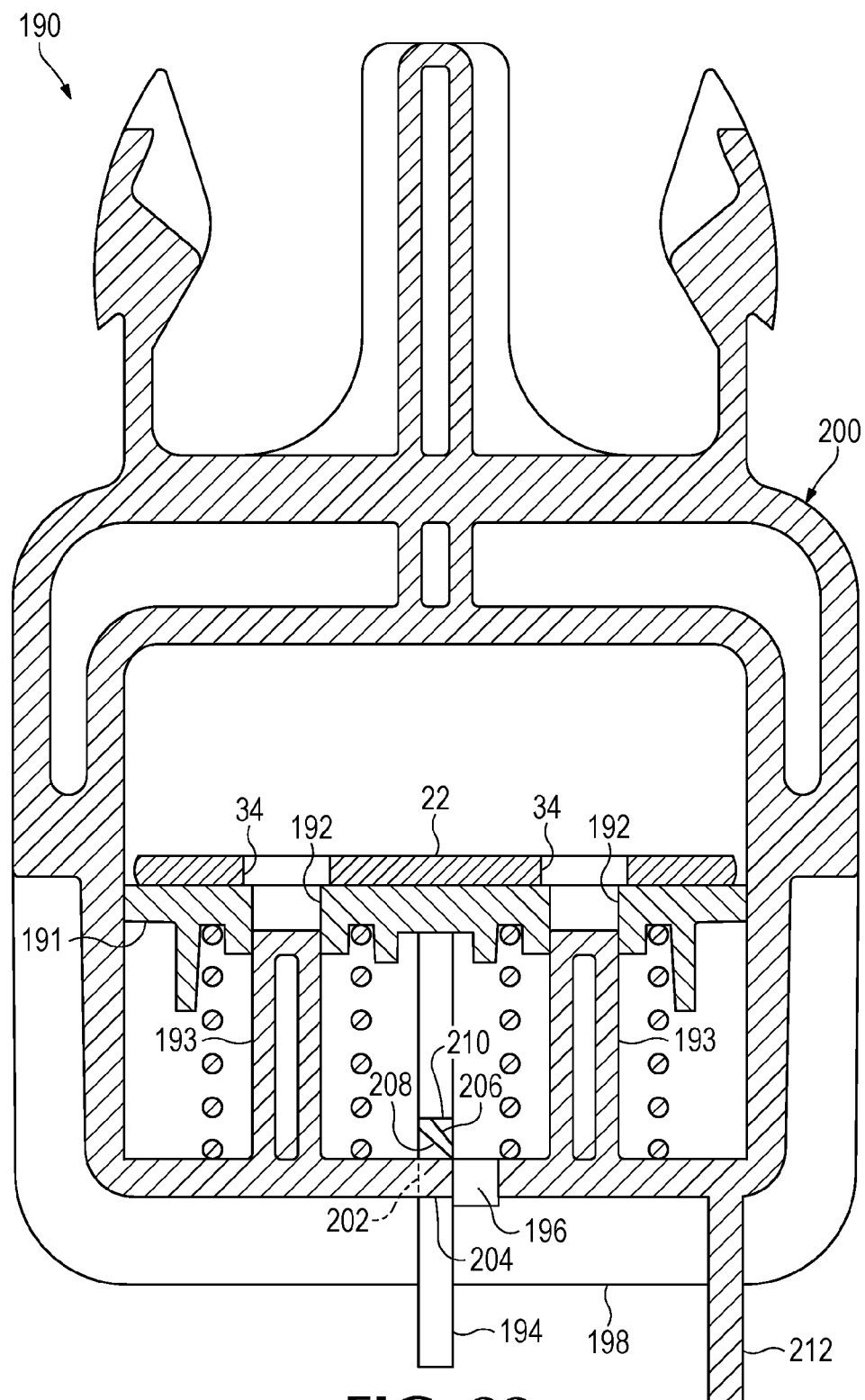
FIG. 22 is a view similar to FIG. 21, but showing the buckle in a relaxed state, as before tension has been applied to the buckle by the strap portion of a tourniquet such as the one shown in FIGS. 1-3.

In particular, in a tourniquet 220 shown in FIGS. 13-15 a ratcheting assembly 108 may include an auxiliary strap in the form of an elongated, toothed ratchet tongue 110 having an inner end 112 attached to the inner end 28 of the strap 22, a short distance from the loop 29 by which the buckle 26 or a side release buckle 102 is attached. The ratchet tongue 110 extends along the strap 22 to an outer end 114 of the ratchet tongue, and an array of ratchet teeth 116 are provided along the ratchet tongue 110. Aligned with the outer end 114 of the ratchet tongue and fastened securely to the strap 22 is a mounting base 118 carrying a lever-operated ratchet mechanism 120. A body 122 of the lever-operated ratchet mechanism defines a passageway through which the ratchet tongue 110 extends movably, and a lever 124 mounted on the body can be pivoted about an axis 126, to move lever teeth 128 into engagement with successive ones of the ratchet teeth 116 and thus to pull the ratchet tongue 110 through the body 122. A spring-loaded retaining pawl 130 keeps ratchet tongue 110 from moving back out of the ratchet body 122 as the ratchet lever 124 is returned to its original position to disengage the lever teeth 128 and permit them to engage other ratchet teeth 116 further along the ratchet tongue 110. The pawl 130 may be released by pulling on a release lever 132 when it is desired to release the tourniquet 20.

Fine Circumferential adjustment of an emergency extremity tourniquet 320 may also be accomplished, as shown in FIGS. 16 and 17, by a tensioning mechanism 140 in which a strong cord or string 142, which may be similar to braided fishing line, of a strong artificial fiber such as Dacron®, for example, may be tightened by a winding mechanism 144 including a spool held by a ratchet. The string may extend from the winding mechanism 144 to the inner end 150 of the strap 22 and be arranged to extend back and forth through several holes to give a mechanical advantage as the string 142 is wound. The winding mechanism 144 may be held in a winder body from which a guide strap 146 extends toward and within a main guide channel 148 along part of the loop formed by the strap 22, as shown with the extremity tourniquet 320 in place upon a patient's limb, in FIG. 16. Thus, tightening the string 142 moves the second, or inner, end 150 of the strap 22 toward the winding mechanism 144. At a side of the winding mechanism opposite the location of the cord, the force-regulating buckle may be attached to the winding mechanism body, either removably, as by a hook 152 engaging the bar 54 of the frame 70 of the force-regulating buckle 26, or, by a more permanent connector (not shown) extending from the winding mechanism 144 to the frame of the force-regulating buckle 26. A winding handle 154 may be attached to a spool shaft of the winding mechanism 144 in a manner allowing the winding handle 154 to be folded flat against a top of the winder mechanism 144, and the winder handle may include a surface 156 on which information can be recorded regarding the identity of the patient and the time of application of the tourniquet.

As another mechanism for providing fine circumference adjustment, a similar emergency extremity tourniquet 420 includes an inflatable bladder 160, as shown in FIGS. 18 and 19, that may be incorporated in or attached to the strap 22 near its inner end 28. A layer 45 of self-engaging fastener material may be provided on the second, or outer, layer 44 of the strap 22. Once the emergency extremity tourniquet 420 is initially applied to the patient's limb, with the force-regulating buckle 26 engaging holes 24 in the strap to establish the baseline tension, and the strap has been secured against movement through the buckle 26 by the layer 45 of fastener material, the bladder 160 may be inflated, using a suitable hand pump 162 or other source of pressurized air (not shown), until the effective internal circumference of the tourniquet 420 has been reduced sufficiently to stanch the hemorrhage.

Where an injury to, for example a lower leg, requires application of a tourniquet to a patient's thigh to stop bleeding, application of the emergency extremity tourniquet 20 disclosed herein gives an emergency caregiver confidence that a baseline tension in the tourniquet has been achieved. Thus, if use of the Spanish windlass winding member 58 or other Fine Circumference adjustment tension-increasing mechanism doesn't stop the bleeding, it is clearly because a second tourniquet is necessary and not because the first tourniquet 20 needs to be removed and reapplied.

As shown in FIGS. 20-24, a buckle 190 is similar in many respects to the buckle 100 shown in FIG. 12 but includes a latch mechanism to retain the sliding block, or slider, 191 in a moved position with respect to the frame 200 of the buckle 190, so that the pins or prongs 193 move to protrude from the holes 192 in the convexly curved strap contact face of the sliding block 191 so that they can be engaged in holes 34 of the strap. Once a predetermined tension has been developed in the strap 22 the sliding block 191 is moved by the tension in the strap 22 to a position with respect to the frame 200 exposing the tips of the pins or prongs 193, and the pins 193 can enter into corresponding holes 34 provided in the strap 22 and keep the main loop of the strap 22 in tension. Upon movement of the slider 191 to a particular position relative to the frame 200, the latch mechanism engages the sliding block 191 and the frame 200 with one another and prevents the sliding block 191 from moving with respect to the frame 200 so as to obscure the prongs 193, even if tension in the strap 22 is relieved so that the tension in the strap would no longer hold the sliding block 191 in its moved position with respect to the frame.

The latch mechanism in the buckle 190 includes a single, centrally located finger 194 that can be moved to release the latch mechanism. The finger 194 is located centrally within the sliding block or slider 191 and extends from the slider 191 and through a centrally located through-hole 196 in the base 198 of the buckle frame 200. A notch 202 is defined at one side of the through-hole 196 and strike faces 204 are located adjacent the notch 202 on each side. Extending on at least one side of the finger 194 and extending on both sides as shown in FIGS. 20-24, a crossbar 206 includes a cam surface 208 to cause the finger 194 to flex and pass through the through-hole, and a latching surface 210 that engages one of the strike faces 204 to engage the latch mechanism and hold the slider 191 in the moved position with respect to the base portion 98 of the frame 200, exposing the pins 193 to protrude from the convex strap contact face.

The latch mechanism is readily released to disengage the slider 191 from the frame 200, so that the slider can move to its original position in which it obscures the pins 193 and allows a strap to slide through the buckle 190.

To assist in unlatching the slider from the latched, or engaged, position of the slider 191, a thumb rest 212 may be provided on one side of the base portion 198, facilitating flexing of the finger 194 to disengage the latch and release the slider 191 to move toward the end of the frame opposite the base 198. The thumb rest 212 also provides a definite indication of which way the finger 194 has to be moved to release it from engagement in the notch 202.

Figure 25:
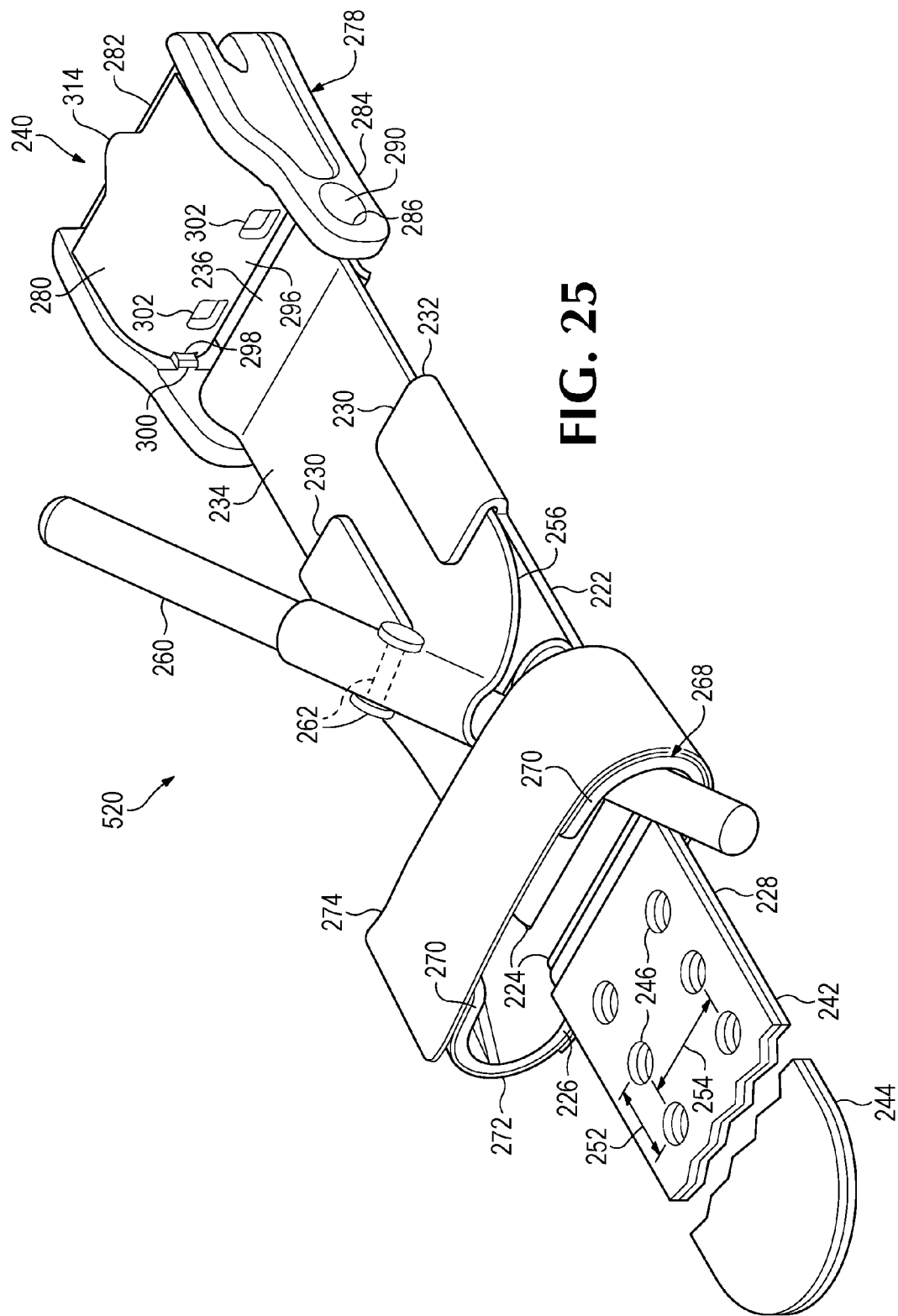
FIG. 25 is an isometric view of a portion of an emergency extremity tourniquet incorporating a latching buckle and otherwise generally similar to the tourniquet shown in FIGS. 1-3, taken from an upper, or outer, side of the tourniquet.
Figure 26:
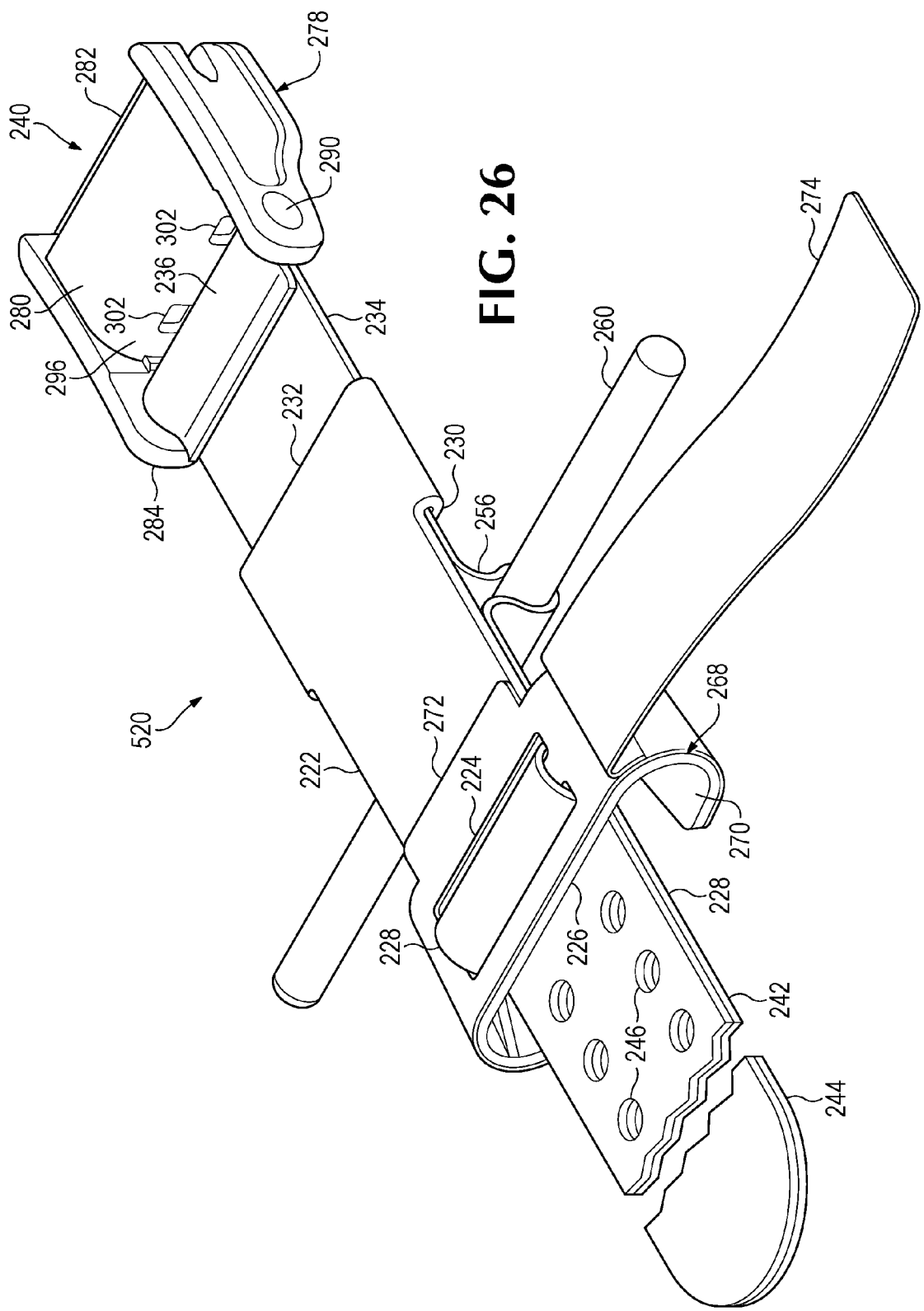
FIG. 26 is an isometric view of the portion of an extremity tourniquet shown in FIG. 25, taken from a lower, or inner, side of the tourniquet.

In FIGS. 25-32 portions of a tourniquet 520 generally similar to the tourniquet 20 shown in FIGS. 1-3 are shown. The illustrated portions of the tourniquet 520 are the ones that interact with one another to fasten and permit adjustment of the tourniquet. As shown in FIGS. 25 and 26 a baseplate 222 includes a pair of parallel transversely-extending slots 224 near an outer end 226, and an elongate strap 228 is threaded through the pair of slots 224. The strap 228, which may be of a sturdy, non-elastic, woven web material, extends along the top of the baseplate 222 and under a pair of retainer guides 230, which may be formed as opposite lateral extensions from the baseplate 222, folded upward and inward toward each other and the midline of the baseplate 222 near the inner end 232 of the baseplate 222. An inner end 234 of the strap 228 may extend a small distance, such as about 10 or 15 cm, beyond the inner end 232 of the baseplate and is permanently fastened as a small loop 236 that attaches the strap to a tension-measuring and setting buckle 240, which will be described in greater detail presently.

A free outer portion 242 of the strap 228 extends away from the outer end 226 of the baseplate 222, as shown in FIGS. 25 and 26. The outer portion 242 of the strap, as in the strap 22 shown in FIGS. 1-3, includes an array of pairs of holes 246 spaced apart from each other along the length of the strap 228. The holes 246 are spaced apart from each other laterally of the strap 228 by a distance corresponding to the spacing between a pair of pins 250 of the buckle 240, and each of the holes 246 is large enough to receive one of the pins 250 comfortably. For example, the longitudinal center-to-center distance 252 between holes 246 may be about 0.5 inch, and the lateral center-to-center distance 254 may be about 0.75 inch.

Similar to the strap 22, the free outer portion 242 of the strap 228 that extends away from the baseplate 222 toward the outer end 244 may be constructed of two layers of strong, flexible, non-elastic fabric. A first layer may be an extension of a portion 256 of the strap 228 extending from the loop 236 and along the baseplate 222. A second layer 258 may be faced with a self-engaging fastening material such as OMNI-TAPE®, Velcro® or with other material or devices that will secure confronting parts of the layer 258 of the strap to each other to prevent relative movement during use of the tourniquet. The portion 256 of the first layer of the strap that extends along the top of the baseplate 222 to the small loop 236 extends around the mid-length portion of a winding member 260, which may be a rod. The portion 256 of the strap may be secured to the winding member 260 by a fastener such as a rivet 262 that extends through a pair of holes defined in the strap portion 256 and a hole that extends through the rod.

A retainer 268 that may be generally similar to the retainer 60 of the tourniquet 20 is provided at the outer end 226 of the base plate 268. The retainer extends transversely with respect to the base plate 222 and includes a pair of arcuately upwardly extending C-shaped hooks 270 each available to receive and hold one of the opposite ends of the winding member 260 when the tourniquet 220 is in use. An area of a first fastening material 272, such as the hook-bearing, or thistle cloth, portion of fastening material such as Velcro®, extends along and is fastened to the outer surface of the retainer 268, as may be seen best in FIG. 26. A retainer strap 274 has an inner face adapted to mate with the first fastening material 272 and thus may be of loop pile material. One end of the retainer strap 274 may be attached securely, as by being glued or thermally welded, to the first fastening material 272. The retainer strap extends along the retainer and is long enough to extend across the gap between the hooks 270 so as to form an enclosure to hold an end of the winding member 260 in the retainer 268 to prevent it from being inadvertently dislodged from within the retainer during use of the tourniquet 220.

The buckle 240 is a force-regulating or tension-measuring and setting buckle, generally similar to the buckle 26 in that it includes the pins 250 that are exposed to engage the holes 246 in the strap once a predetermined amount of tension in the strap 228 is applied to the buckle 240.

As shown in FIGS. 27-31, the buckle 240 may include a rigid frame assembly 278 and a sliding block 280 that may also be referred to as a slider. The frame assembly 278 includes a main portion including a base 282 from which a pair of parallel arms 284 extend at respective sides of the base. Openings 286, 288 are defined in an outer end of each of the parallel arms 284, and a bar 290 fits in the openings, interconnecting the parallel arms 284. The opening 286 may be larger than the opening 288, and one end of the bar 290 may be enlarged, while the other end may include a protruding ring so that the bar may fit into the openings 286, 288 with an interference fit at each end. The bar extends through the small loop 236 of the strap 228 to secure the strap to the buckle and enclose an opening for the strap 228 to pass through the buckle 240.

Figure 31:
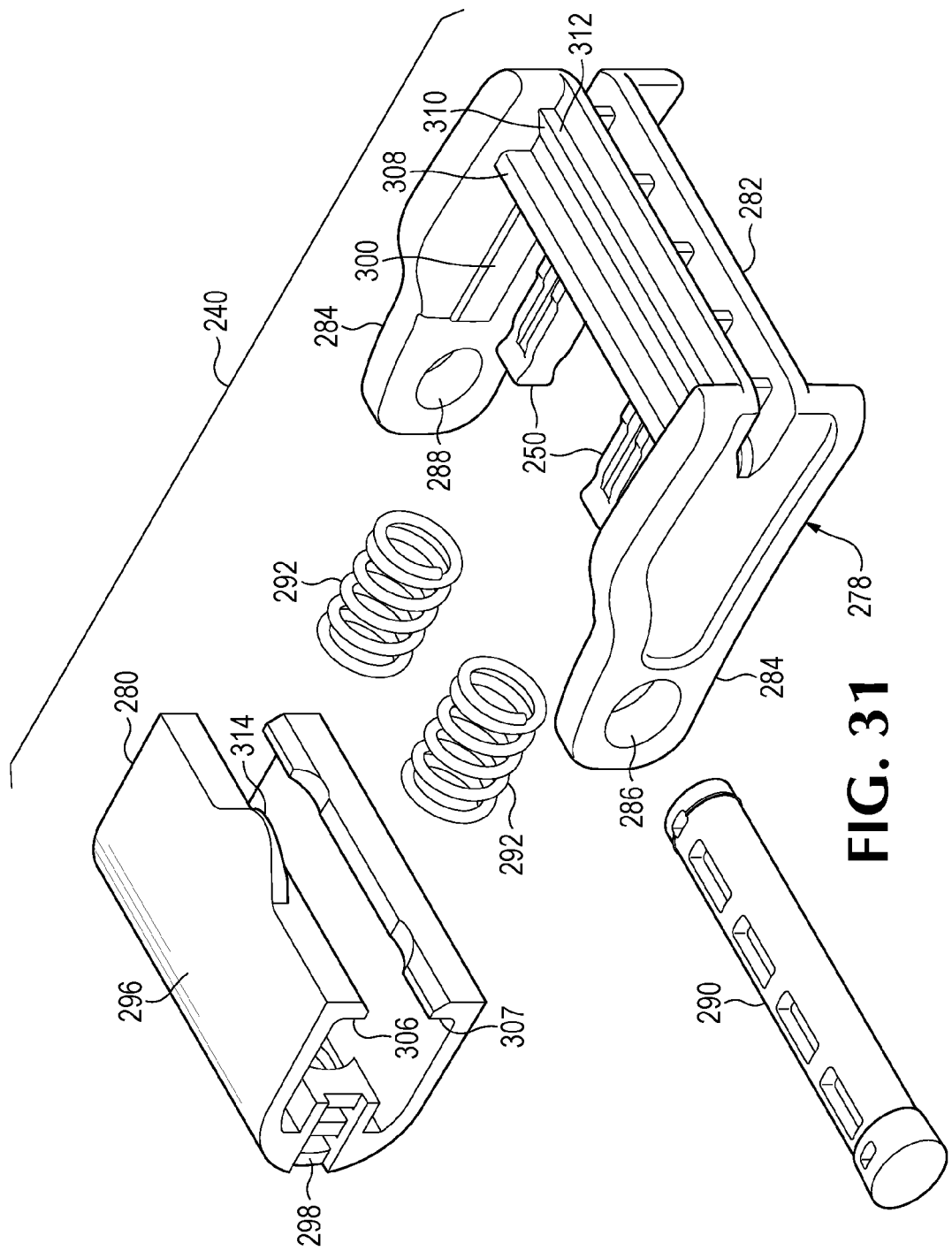
FIG. 31 is an exploded isometric view of the buckle shown in FIGS. 25-30.

The pins 250 extend from the base 282 between and parallel with the arms 284 and may be molded integrally with the base. A pair of helical springs 292 may fit around and extend along the lower portions of the pins 250, adjacent the base 282. The sliding block, or slider 280, is of a generally U-shaped configuration, as seen in FIGS. 29, 30, and 31, and fits between the parallel arms 284 of the buckle 240. It has a convex curved strap contact face 296 similar to the face 76 of the sliding block 72. The sliding block 280 defines grooves 298 that receive ribs 300 extending along the inner faces of the parallel arms 284 to guide the sliding block 280 and keep it properly aligned with the frame assembly 278. The curved face 296 of the sliding block includes a pair of holes 302 aligned with the pins 250 so that they may extend into and through the holes 302. The sliding block 280 may include seats 304 surrounding the holes 302 on an inner side of the sliding block 280 to allow the springs 292 to act on the sliding block 280, urging it away from the base 282 of the buckle frame, as shown in FIGS. 27-31.

As with the buckle 26, the sliding block 280 may be molded or otherwise formed from a suitable elastic material such as a resilient and tough but generally rigid plastics material and includes retaining lips 306, 307 that engage flanges 308 on the base 282 of the frame as shown in FIG. 29.

The buckle 240 includes a latch mechanism to keep the sliding block 280 in a position with respect to the base 280 in which the pins 250 extend through and beyond the curved face 296 to be able to engage holes 246 in the strap 228. As part of the latch mechanism, on a front, or upper, side of the base 282 of the buckle there is a catch 310 in the form of a ramp extending transversely along the base 282. When the sliding block 280 has been urged toward the base 282 by tension in the strap, a cam face 311 on the retaining lip 306 can ride up along the ramp of the catch 310 and then engage a face 312 of the catch 310 as shown in FIG. 30. The elasticity of the sliding block continues to urge the adjacent retaining lip 306 inward toward the base 282 so as to rest alongside the face 312 of the catch 310 and thus to hold the sliding block 280 in the position shown in FIG. 30, where the pins 250 extend outwardly through the holes 302 and are thus available to engage and remain engaged in respective ones of the holes 246 in the strap 228, once sufficient tension in the strap 228 has been reached. The buckle 240 thus ensures that the loop of the strap 228 is tightened to the value determined to be sufficient as a gross circumference adjustment when the tourniquet is initially put into place around a patient's limb. Since the catch 310 extends along the width of the base 282 the lip 306 can engage the entire catch 310 and sliding block 280 is not subject to being held at only one side of the base 282. As a result, the latch mechanism is either fully latched or clearly not latched.

A release tab 314 extends from the front or upper side of the sliding block, where retaining lip 306 engages the catch 310, to permit the sliding block 280 to be released at an appropriate time for removing the tourniquet 220 from the patient.

With the sliding block 280 kept latched to the base 282 of the buckle 240 the pins 250 extend through the sliding block 280 and remain available to engage the holes 246 in the strap 228. A person applying the tourniquet 220 then can easily secure the face of the layer 258 in the part 243 of the outer portion 242 of the strap 228 that extends through and away from the buckle 240, to the layer 258 of the part of the outer portion 242 of the strap forming the loop around the patient's limb and extending to the buckle 240, by use of the fastening material of the second layer 258 of the strap 228.

When the part 243 of the strap 228 extending from the buckle 240 has been secured to the part of the outer portion 242 of the strap forming the loop around a patient's limb the part 243 of the strap covers the release tab 314 and shields it against inadvertent contact that might result in the sliding block 280 being released from being latched to the base 282 of the frame assembly 278 and then being pushed by the springs 292 toward a position in which the pins 250 could be obscured by the sliding block 280. As shown in FIG. 32, however, once the outer part 243 of the strap 228 is separated from the part of the outer portion 242 of the strap 228 forming the loop around the patient's limb the release tab 314 is exposed and can be moved away from the base 282 in the direction of the arrow 316 to disengage the retainer lip 306 from the latch face 312 of the catch 310.

Employment of the tourniquet 220 is essentially similar to that described previously with respect to the tourniquet 20. The winding member, used as a Spanish windlass, increases the tension and shortens the effective length of the portion 256 of the strap 228 between the slots 224 and the loop 236 in the inner end 234 of the strap, thus pulling the inner end portion of the strap through, between and under the retainer guides 230 at the inner end 232 of the baseplate 222. Further winding of the Spanish windlass can then pull more of the strap 228 through the slots 224, further tightening the loop around the patient's limb. When sufficient tension has been established by use of the Spanish windlass one of the ends of the winding member 260 is engaged with one of the C-shaped hooks 270 of the retainer 268 and may be secured by use of the retainer strap 274 to prevent inadvertent release of tension during transport or other care of the patient once the tourniquet 220 has been installed.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A buckle, comprising:
    (a) a frame having a base portion and a pair of opposite sides and defining an opening through the frame from one to the other of the opposite sides;
    (b) a movable member disposed within the opening through the frame and movable between a first position with respect to the frame, in which the movable member shields an engagement member, and a second position with respect to the frame, in which at least a portion of the engagement member is exposed and extends proud of a surface of the movable member;
    (c) a resiliently compressible member urging the movable member toward the first position; and
    (d) a latch capable of overcoming the urging of the compressible member entirely without assistance, and arranged to be engaged automatically and thus to hold the movable member in the second position with respect to the frame, in response to the movable member moving into the second position.

2. The buckle of claim 1, wherein the compressible member is a spring that acts on the movable member with a predetermined force urging the movable member toward the first position.

3. The buckle of claim 1, wherein the movable member is a slider having a strap contact face, and wherein the frame and the slider together define a passageway adapted to receive a strap extending through the opening, along and in contact with the strap contact face of the slider.

4. The buckle of claim 3, wherein the slider defines a hole through the strap contact face and the engagement member is a pin mounted on the base portion of the frame and aligned with the hole, the pin protruding through the hole and proud of the strap contact face of the slider when the slider is in the second position with respect to the base portion of the frame.

5. The buckle of claim 1 wherein the base portion of the frame includes a protruding retainer flange on each of the opposite sides of the frame;
    wherein the movable member is a slider including a pair of opposite side portions each corresponding to a respective one of the opposite sides of the frame;
    wherein each of the opposite side portions of the slider includes a respective inwardly-directed retainer lip located facing an exterior side of the respective retainer flange so as to keep the slider in place on the frame;
    wherein the slider is of an elastic material flexible and resilient enough for the opposite side portions of the slider to be separated from each other far enough for the retainer lips to pass over the retainer flanges and thereafter to keep the retainer lips in position to engage the retainer flanges; and
    wherein the latch includes a ramp and a latch face located in position to be engaged by one of the retainer lips to hold the slider when the slider has been moved to the second position.

6. A buckle, comprising:
    (a) a frame having a base portion that defines a through-hole and having a pair of opposite sides and defining an opening through the frame from one to the other of the opposite sides;
    (b) a movable member that is a slider that includes a finger extending through the through-hole, the movable member being disposed within the opening through the frame and movable between a first position with respect to the frame, in which the movable member shields an engagement member, and a second position with respect to the frame, in which at least a portion of the engagement member is exposed and extends proud of a surface of the movable member;
    (c) a catch protruding from the finger;
    (d) a resiliently compressible member urging the movable member toward the first position;
    (e) a latch arranged to be engaged automatically and to hold the movable member in the second position with respect to the frame, in response to the movable member moving into the second position; and
    (f) a latch strike surface located on the base portion where it can be engaged by the catch when the slider moves into the second position with respect to the base portion, and wherein the finger is elastically biased to urge the catch into engagement with the latch strike surface.

7. A buckle, comprising:
    (a) a frame having a base portion and a pair of opposite sides and defining an opening through the frame from one to the other of the opposite sides, the base portion of the frame including a protruding retainer flange on each of the opposite sides of the frame;
    (b) a slider disposed within the opening through the frame and movable between a first position with respect to the frame, in which the slider shields an engagement member, and a second position with respect to the frame, in which at least a portion of the engagement member is exposed and extends proud of a surface of the slider, the slider including a pair of opposite side portions each corresponding to a respective one of the opposite sides of the frame, and each of the opposite side portions of the slider including a respective inwardly-directed retainer lip located facing an exterior side of the respective flange so as to keep the slider in place on the frame, and the slider being of an elastic material that is flexible and resilient enough for the opposite side portions of the slider to be separated from each other far enough for the retainer lips to pass over the retainer flange and thereafter to keep the retainer lips in position to engage the retainer flange;
    (c) a resiliently compressible member urging the slider toward the first position; and
    (d) a latch arranged to be engaged automatically and to hold the slider in the second position with respect to the frame, in response to the slider moving into the second position, and wherein the latch includes a ramp and a latch face located in position to be engaged by one of the retainer lips to hold the slider when the slider has been moved to the second position, and including a latch release tab mounted on the slider in a position to facilitate pulling the one of the retainer lips away from the latch and thereby releasing the slider from the second position.

8. A tourniquet for occluding hemorrhage in a distal portion of a person's limb, comprising;
(a) an elongate flexible tension-bearing member having a pair of opposite ends and including a portion available to be formed into a loop around the person's limb;
(b) a tension-measuring mechanism, arranged to sense tension in a portion of the tension-bearing member that has been formed into the loop;
(c) a first fastening mechanism arranged to engage a portion of the tension-bearing member, in response to sensing at least a baseline first amount of tension in the portion of the tension-bearing member forming the loop, and to retain the tension-bearing member thereafter so as to maintain the first amount of tension in the loop extending around the person's limb, the first fastening mechanism including a movable member arranged to move from a first position to a second position in response to sensing the baseline first amount of tension;
(d) a tension-increasing mechanism associated with the tension-bearing member and operable when the baseline amount of tension has been established in the loop by the first fastening mechanism, to increase tension in the loop beyond the baseline amount; and
(e) a latch associated with the first fastening mechanism and arranged to be engaged automatically in response to the movable member being in the second position and to keep the movable member of the first fastening mechanism in the second position without assistance from the flexible tension-bearing member.

9. The tourniquet of claim 8 including a second fastening mechanism associated with the tension-increasing mechanism, operable to retain a status of increased tension established by the tension-increasing mechanism, once an increased tension has been attained.

10. The tourniquet of claim 8 wherein the tension-measuring mechanism is included in a buckle.

11. The tourniquet of claim 10 wherein the tension-bearing member includes a strap, wherein there are a plurality of holes spaced apart from one another along a length of the strap, and wherein the buckle includes a pin arranged to engage one of the plurality of holes only after the baseline tension has been attained.

12. The tourniquet of claim 10 wherein the tension-bearing member includes a strap that defines at least one hole, wherein the buckle includes a base portion, and wherein the movable member is a slide portion and wherein the buckle has at least one pin projecting from the base portion, the slide portion having a strap contact face and being mounted over the at least one pin and being movable relative to the base portion, and the slide portion being urged by a spring to remain in a non-engaging position in which the at least one pin does not project beyond the strap contact face of the slide portion, until tension in the strap opposing the spring moves the slide portion toward the base portion to a strap-engaging position in which at least one pin projects beyond the strap contact face of the slide portion and can engage said at least one hole in the strap, thereby establishing a position of the strap with respect to the buckle and establishing a baseline amount of tension in the loop, and wherein the latch is arranged to hold the slide portion in the strap-engaging position in which the at least one pin projects from the strap contact face of the slide portion.

13. The tourniquet of claim 8 wherein the tension-increasing mechanism is a Spanish windlass including a winding member attached to the tension-bearing member and operable effectively to shorten the portion of the tension-bearing member forming the loop.

14. The tourniquet of claim 8 wherein the tension-increasing mechanism acts to reduce the size of the loop and thus to increase the compressing effect of the tourniquet on a person's limb.

15. The tourniquet of cairn 8 wherein the tension-increasing mechanism includes an auxiliary strap connected with the tension-bearing member, a ratchet mechanism, a lever included in the ratchet mechanism and operable to increase tension in the auxiliary strap, and a pawl included in the ratchet mechanism to hold and retain tension in the auxiliary strap.

16. The tourniquet of claim 8 wherein the tension-increasing mechanism includes an inflatable bladder associated with the flexible tension-bearing member and located so as to be retained within the loop, whereby inflating the bladder causes the bladder to occupy a portion of a space encircled by the loop and thereby increases tension in the loop and acts to help occlude a blood vessel in the limb of the person.

17. A tourniquet for occluding hemorrhage in a distal portion of a person's limb, comprising:
(a) an elongate flexible tension-bearing member including a strap and having a pair of opposite ends and including a portion available to be formed into a loop around the person's limb;
(b) a tension-measuring mechanism, included in a buckle and arranged to sense tension in a portion of the tension-bearing member that has been formed into the loop;
(c) a first fastening mechanism arranged to engage a portion of the tension-bearing member, in response to the tension-measuring mechanism sensing at least a baseline first amount of tension in the portion of the tension-bearing member forming the loop, and to retain the tension-bearing member thereafter so as to maintain the first amount of tension in the loop extending around the person's limb, the first fastening mechanism including a movable member arranged to move from a first position to a second position in response to sensing the baseline first amount of tension and wherein there are a plurality of holes spaced apart from one another along a length of the strap, and wherein the buckle includes a pin arranged to engage one of the plurality of holes only after the baseline tension has been attained;
(d) a tension-increasing mechanism associated with the tension-bearing member and operable when the baseline amount of tension has been established in the loop by the first fastening mechanism, to increase tension in the loop beyond the baseline amount;
(e) a latch associated with the first fastening mechanism and arranged to be engaged in response to the movable member being in the second position and to keep the movable member of the first fastening mechanism in the second position; and
(f) a quick-release connector attached to an end of the tension-bearing member, the buckle being releasably connected to the quick-release connector.

18. A tourniquet for occluding hemorrhage in a distal portion of a person's limb, comprising:
(a) an elongate flexible tension-bearing member having a pair of opposite ends and including a portion available to be formed into a loop around the person's limb;

(b) a tension-measuring mechanism, arranged to sense tension in a portion of the tension-bearing member that has been formed into the loop;

(c) a first fastening mechanism arranged to engage a portion of the tension-bearing member, in response to sensing at least a baseline first amount of tension in the portion of the tension-bearing member forming the loop, and to retain the tension-bearing member thereafter so as to maintain the first amount of tension in the loop extending around the person's limb, the first fastening mechanism including a movable member arranged to move from a first position to a second position in response to sensing the baseline first amount of tension;

(d) a tension-increasing mechanism associated with the tension-bearing member and operable when the baseline amount of tension has been established in the loop by the first fastening mechanism, to increase tension in the loop beyond the baseline amount, the tension-increasing mechanism including a flexible cord and a winding mechanism including a ratchet arranged to maintain tension in the cord, the tension-increasing mechanism having a pair of opposite ends, one of which is connected to the tension-bearing member of the tourniquet at a respective location near a first end of the tension bearing member; and (e) a latch associated with the first fastening mechanism and arranged to be engaged in response to the movable member being in the second position and to keep the movable member of the first fastening mechanism in the second position.

19. A method of applying a tourniquet, comprising:

(a) wrapping an elongate flexible tension-bearing member around a patient's limb;

(b) passing a portion of the flexible tension-bearing member through a tension-measuring and setting buckle connected with another part of the tension-bearing member, thereby forming a loop around the limb;

(c) thereafter, pulling the flexible tension-bearing member through the buckle, thereby increasing tension in the loop until tension in the loop reaches a baseline value and moves a movable member of the buckle to a baseline tension setting position enabling the buckle to be engaged with the flexible tension-bearing member;

(d) once the tension-measuring and setting buckle determines that the predetermined baseline amount of tension has been attained, latching the movable member of the tension-measuring and setting buckle in the baseline tension setting position, securely enough that the latch would hold the movable member in the baseline tension setting position thereafter without tension being maintained in the loop;

(e) with the movable member latched in the baseline tension setting position, engaging the buckle with the flexible tension-bearing member and thereby retaining the baseline amount of tension in the loop; and (f) thereafter using a tension-increasing mechanism separate from the buckle to increase tension in the flexible tension-bearing member, thereby increasing tension in the loop to an amount greater than the baseline tension, and thereby reducing the circumference of the loop, until the tourniquet is satisfactorily tight.

* * * * *